(12) United States Patent
Huffman

(10) Patent No.: US 7,690,919 B2
(45) Date of Patent: Apr. 6, 2010

(54) DENTAL ARTICULATOR

(76) Inventor: Ronald E. Huffman, P.O. Box 68440, Oro Valley, AZ (US) 85737

( * ) Notice: Subject to any disclaimer, the term of this patent is extended or adjusted under 35 U.S.C. 154(b) by 247 days.

(21) Appl. No.: 11/390,604

(22) Filed: Mar. 28, 2006

(65) Prior Publication Data

US 2007/0231770 A1  Oct. 4, 2007

(51) Int. Cl.
*A61C 11/00* (2006.01)
(52) U.S. Cl. .......................... 433/60; 433/54
(58) Field of Classification Search ............ 433/33–34, 433/53–54, 57, 60, 64, 74, 214
See application file for complete search history.

(56) References Cited

U.S. PATENT DOCUMENTS

| | | | |
|---|---|---|---|
| 603,803 A | 5/1898 | White | |
| 921,791 A | 5/1909 | Benson | |
| 967,086 A | 8/1910 | Tuttle | |
| 1,013,028 A | 12/1911 | Lee | |
| 1,204,166 A | 11/1916 | Levin | |
| 1,314,223 A | 8/1919 | Sorensen | |
| 1,553,492 A | 9/1925 | Williams | |
| 1,745,570 A | 2/1930 | Dimelow | |
| 1,772,027 A | 8/1930 | Baumgarten | |
| 1,780,117 A | 10/1930 | Craigo | |
| 2,031,996 A | 2/1936 | Zelesnick | |
| 2,037,344 A | 4/1936 | Schwartz | |
| 2,234,411 A | 3/1941 | McDonald | |
| 2,376,384 A | 5/1945 | Ringle et al. | |
| 2,398,671 A | 4/1946 | Saffir | |
| 2,577,420 A | 12/1951 | Jablonski et al. | |
| 2,585,857 A | 2/1952 | Schwartz | |
| 2,608,762 A | 9/1952 | Fox | |
| 2,613,440 A | 10/1952 | Murray et al. | |
| 2,621,407 A | 12/1952 | Schlesinger | |
| 2,669,780 A | 2/1954 | Mann | |
| 2,758,374 A | 8/1956 | Fisher et al. | |
| 2,765,533 A | 10/1956 | McMorris | |
| 2,827,899 A | 3/1958 | Altieri | |
| 2,842,845 A | 7/1958 | Carlson | |
| 2,963,786 A | 12/1960 | Browning | |

(Continued)

FOREIGN PATENT DOCUMENTS

CA  117628  11/2007

(Continued)

OTHER PUBLICATIONS

U.S. Appl. No. 29/216,696, filed Nov. 5, 2004.

(Continued)

*Primary Examiner*—Cris L Rodriguez
*Assistant Examiner*—Matthew M Nelson
(74) *Attorney, Agent, or Firm*—Holland & Hart, LLP

(57) ABSTRACT

A dental modeling system for forming a dental model from a mold of at least a portion of a person's opposed upper and lower teeth. The modeling system includes dental articulator features that are integrated with opposing bases and dental model bases configured to receive removable tapered pins. The system also includes pin locators for improved alignment of teeth of the dental mold when creating the dental model. The pin locator can also include removable tapered pins for use in aligning with specific teeth of the dental mold.

26 Claims, 27 Drawing Sheets

U.S. PATENT DOCUMENTS

| | | |
|---|---|---|
| 3,150,448 A | 9/1964 | Wozar |
| 3,236,235 A | 2/1966 | Jacobs |
| 3,247,844 A | 4/1966 | Berghash |
| D210,278 S | 2/1968 | White |
| 3,416,527 A | 12/1968 | Hoef |
| 3,453,736 A | 7/1969 | Waltke |
| 3,454,256 A | 7/1969 | Stern |
| 3,461,562 A | 8/1969 | Cooper |
| 3,478,428 A | 11/1969 | Stengel |
| 3,498,580 A | 3/1970 | Wilson |
| 3,510,947 A | 5/1970 | Tuccillo |
| 3,518,761 A | 7/1970 | Susman et al. |
| 3,552,018 A | 1/1971 | Zahn |
| 3,581,398 A | 6/1971 | Thomas |
| 3,650,032 A | 3/1972 | Kestler |
| 3,753,291 A | 8/1973 | Bocian et al. |
| 3,815,236 A | 6/1974 | Cooper |
| 3,832,777 A | 9/1974 | Tinder |
| 3,913,230 A | 10/1975 | Weiss |
| 3,934,348 A | 1/1976 | Janjic |
| 3,937,773 A | 2/1976 | Huffman |
| 3,947,964 A | 4/1976 | Lee |
| 3,969,820 A | 7/1976 | Kulig et al. |
| 4,021,916 A | 5/1977 | Spalten |
| 4,022,419 A | 5/1977 | Haker |
| 4,116,416 A | 9/1978 | Segura |
| 4,122,606 A | 10/1978 | Roman |
| 4,127,939 A | 12/1978 | Samuel et al. |
| 4,169,314 A | 10/1979 | Mercer et al. |
| 4,174,570 A | 11/1979 | Schwartz |
| 4,203,219 A | 5/1980 | Wiener |
| D257,387 S | 10/1980 | Skarky |
| 4,229,167 A | 10/1980 | Kikuchi et al. |
| 4,240,605 A | 12/1980 | Waltke |
| 4,242,812 A | 1/1981 | Randoll et al. |
| 4,265,619 A | 5/1981 | Lucki et al. |
| 4,283,173 A | 8/1981 | Browne et al. |
| 4,301,357 A | 11/1981 | Huffman |
| 4,315,740 A | 2/1982 | Mercer et al. |
| 4,319,875 A | 3/1982 | Beckwith |
| 4,359,464 A | 11/1982 | Weinstock |
| 4,371,339 A | 2/1983 | Zeiser |
| 4,378,929 A | 4/1983 | Huffman |
| 4,382,787 A | 5/1983 | Huffman |
| 4,398,884 A | 8/1983 | Huffman |
| 4,403,961 A | 9/1983 | Gurney |
| 4,436,511 A | 3/1984 | Mitchell, Sr. |
| 4,439,151 A | 3/1984 | Whelan |
| 4,443,192 A | 4/1984 | Blitz |
| 4,449,930 A | 5/1984 | Huffman |
| 4,449,931 A | 5/1984 | Saito |
| 4,459,110 A | 7/1984 | Jackson |
| 4,460,338 A | 7/1984 | Mercer et al. |
| 4,473,353 A | 9/1984 | Greggs |
| 4,481,162 A | 11/1984 | Huffman |
| 4,494,934 A | 1/1985 | Huffman |
| 4,504,226 A | 3/1985 | Gordon |
| D278,274 S | 4/1985 | Levine |
| 4,521,188 A | 6/1985 | Metzler |
| 4,533,323 A | 8/1985 | Huffman |
| 4,538,987 A | 9/1985 | Weissman |
| 4,548,581 A | 10/1985 | Huffman |
| D283,541 S | 4/1986 | Huffman |
| D283,542 S | 4/1986 | Huffman |
| D283,639 S | 4/1986 | Huffman |
| D283,730 S | 5/1986 | Huffman |
| 4,608,016 A | 8/1986 | Zeiser |
| D286,179 S | 10/1986 | Huffman |
| D286,436 S | 10/1986 | Huffman |
| 4,645,454 A | 2/1987 | Amdur et al. |
| D289,924 S | 5/1987 | Huffman |
| 4,671,770 A | 6/1987 | Bell et al. |
| 4,708,648 A | 11/1987 | Weissman |
| 4,708,835 A | 11/1987 | Kiefer |
| 4,721,464 A | 1/1988 | Roden et al. |
| 4,734,033 A | 3/1988 | Huffman |
| D295,314 S | 4/1988 | Kwok |
| 4,767,330 A | 8/1988 | Burger |
| 4,767,331 A | 8/1988 | Hoe |
| 4,786,253 A | 11/1988 | Morais |
| 4,834,651 A | 5/1989 | Fenick |
| 4,842,242 A | 6/1989 | Huffman |
| D302,456 S | 7/1989 | Huffman |
| D302,587 S | 8/1989 | Huffman |
| D302,724 S | 8/1989 | Huffman |
| D302,725 S | 8/1989 | Huffman |
| 4,865,546 A | 9/1989 | Naylor |
| RE33,099 E | 10/1989 | Shoher et al. |
| 4,886,453 A | 12/1989 | Ludwigs |
| D305,361 S | 1/1990 | Huffman |
| D305,362 S | 1/1990 | Huffman |
| D306,206 S | 2/1990 | Huffman |
| 4,898,359 A | 2/1990 | Gopon |
| 4,917,347 A | 4/1990 | Fenick |
| RE33,271 E | 7/1990 | Shoher et al. |
| 4,940,409 A | 7/1990 | Nordin |
| 4,941,827 A | 7/1990 | Mack |
| 4,980,124 A | 12/1990 | Dimmer |
| D315,209 S | 3/1991 | Mann |
| D315,955 S | 4/1991 | Mann |
| 5,015,182 A | 5/1991 | Newberry |
| 5,028,235 A | 7/1991 | Smith |
| 5,044,949 A | 9/1991 | Xanthopoulos |
| 5,049,075 A | 9/1991 | Barrut |
| 5,076,789 A | 12/1991 | Tanaka |
| D323,559 S | 1/1992 | Shafer |
| 5,098,290 A | 3/1992 | Honstein et al. |
| 5,100,317 A | 3/1992 | Darnand |
| 5,197,874 A | 3/1993 | Silva et al. |
| 5,207,574 A | 5/1993 | Garland |
| 5,222,891 A | 6/1993 | Poveromo |
| 5,352,117 A | 10/1994 | Silva |
| 5,393,227 A | 2/1995 | Nooning |
| 5,403,185 A | 4/1995 | Presswood |
| 5,466,152 A | 11/1995 | Walter |
| 5,470,231 A | 11/1995 | Stern |
| 5,501,600 A | 3/1996 | Johnson |
| 5,586,884 A | 12/1996 | Kraus |
| 5,597,303 A | 1/1997 | Simmons |
| 5,622,497 A | 4/1997 | Cho |
| 5,645,425 A | 7/1997 | Callne |
| 5,658,143 A | 8/1997 | Kuperman |
| 5,722,828 A | 3/1998 | Halstrom |
| 5,766,007 A | 6/1998 | Huffman |
| 5,769,634 A | 6/1998 | Choi |
| 5,775,899 A | 7/1998 | Huffman |
| 5,788,489 A | 8/1998 | Huffman |
| 5,788,490 A | 8/1998 | Huffman |
| 5,800,166 A | 9/1998 | Huffman |
| 5,807,099 A | 9/1998 | Johnson |
| 5,868,138 A | 2/1999 | Halstrom |
| 5,868,569 A | 2/1999 | Huffman |
| D408,919 S | 4/1999 | Cooley |
| 5,934,901 A | 8/1999 | Huffman |
| 5,970,981 A | 10/1999 | Ochel |
| 5,996,963 A | 12/1999 | Michael |
| 6,033,221 A | 3/2000 | Tsubota et al. |
| D429,815 S | 8/2000 | Huffman |
| D430,672 S | 9/2000 | Huffman |
| D433,136 S | 10/2000 | Huffman |
| D433,754 S | 11/2000 | Huffman |
| 6,149,428 A | 11/2000 | Mogensen |
| 6,186,781 B1 | 2/2001 | Iba |
| 6,193,511 B1 | 2/2001 | Hudson |

| | | | | | | |
|---|---|---|---|---|---|---|
| 6,234,794 B1 | 5/2001 | Ozaki | | D573,712 S | 7/2008 | Huffman |
| D443,363 S | 6/2001 | Huffman | | D575,404 S | 8/2008 | Huffman |
| D444,559 S | 7/2001 | Huffman | | D575,873 S | 8/2008 | Huffman |
| D452,009 S | 12/2001 | Huffman | | D576,732 S | 9/2008 | Huffman |
| D452,010 S | 12/2001 | Huffman | | D576,733 S | 9/2008 | Huffman |
| D452,319 S | 12/2001 | Huffman | | D576,734 S | 9/2008 | Huffman |
| D452,320 S | 12/2001 | Huffman | | 7,425,129 B2 | 9/2008 | Garland |
| D452,321 S | 12/2001 | Huffman | | 7,435,084 B2 | 10/2008 | Liu et al. |
| D452,322 S | 12/2001 | Huffman | | D582,559 S | 12/2008 | Khawaled et al. |
| D452,566 S | 12/2001 | Huffman | | 2002/0102514 A1 | 8/2002 | Huffman |
| D452,567 S | 12/2001 | Huffman | | 2003/0207230 A1* | 11/2003 | Garland ............ 433/60 |
| D452,568 S | 12/2001 | Huffman | | 2004/0013998 A1* | 1/2004 | Jung et al. ............ 433/57 |
| 6,364,661 B1 | 4/2002 | Brattesani | | 2004/0023185 A1* | 2/2004 | Gittleman ............ 433/34 |
| D456,902 S | 5/2002 | Huffman | | 2004/0029070 A1 | 2/2004 | Huffman |
| D456,903 S | 5/2002 | Huffman | | 2004/0029071 A1* | 2/2004 | Huffman ............ 433/74 |
| D456,904 S | 5/2002 | Huffman | | 2004/0096802 A1 | 5/2004 | Gittleman |
| D457,243 S | 5/2002 | Huffman | | 2004/0197729 A1 | 10/2004 | Honstein et al. |
| D457,636 S | 5/2002 | Huffman | | 2005/0064364 A1 | 3/2005 | Huffman |
| D457,637 S | 5/2002 | Huffman | | 2005/0064365 A1 | 3/2005 | Huffman |
| D457,963 S | 5/2002 | Huffman | | 2005/0064366 A1 | 3/2005 | Huffman |
| D457,964 S | 5/2002 | Huffman | | 2005/0106530 A1 | 5/2005 | Huffman |
| 6,425,759 B1 | 7/2002 | Cronin | | 2006/0281043 A1 | 12/2006 | Huffman |
| D464,431 S | 10/2002 | Huffman | | 2007/0037115 A1* | 2/2007 | Sim ............ 433/57 |
| D464,432 S | 10/2002 | Huffman | | 2007/0231770 A1 | 10/2007 | Huffman |
| D464,732 S | 10/2002 | Huffman | | | | |
| D464,733 S | 10/2002 | Huffman | | | | |
| D465,027 S | 10/2002 | Huffman | | | | |

FOREIGN PATENT DOCUMENTS

| | | |
|---|---|---|
| CA | 117629 | 11/2007 |
| DE | 3 436 094 A1 | 3/1985 |
| DE | 3 505 680 A1 | 7/1985 |
| DE | 3 521 137 A1 | 12/1986 |
| DE | 3 825 014 A1 | 1/1990 |
| DE | 295 06 480 U1 | 8/1995 |
| DE | 296 13 916 U1 | 1/1998 |
| DE | 4 01 05 710.0 | 10/2001 |
| EP | 0 210 484 A2 | 2/1985 |
| EP | 0 151 086 A2 | 8/1985 |
| EP | 0 277 026 A2 | 8/1988 |
| EP | 0 291 821 A1 | 11/1988 |
| EP | 0 528 335 A1 | 2/1993 |
| FR | 2 750 851 A1 | 1/1998 |
| FR | 2 757 372 A1 | 6/1998 |
| FR | 2 770 994 | 5/1999 |
| FR | 653652TO653664 | 2/2002 |
| GB | 866118 | 4/1961 |
| GB | 886118 | 1/1962 |
| GB | 2102229 A | 1/1983 |
| GB | 2105427 | 3/1983 |
| GB | 1014814 | 2/1984 |
| GB | 1053786 | 4/1989 |
| GB | 2075293 | 9/1998 |
| GB | 2101077 | 4/2001 |
| JP | 58-147508 | 10/1983 |
| JP | 10-309989 | 11/1998 |
| JP | 1175348 | 4/2003 |
| JP | 1178837 | 5/2003 |
| WO | WO 88/10101 | 12/1988 |
| WO | WO 97/16130 | 5/1997 |
| WO | WO 01/01881 A2 | 1/2001 |

| | | |
|---|---|---|
| 6,471,513 B1 | 10/2002 | Huffman |
| D468,018 S | 12/2002 | Huffman |
| D468,431 S | 1/2003 | Huffman |
| D468,432 S | 1/2003 | Huffman |
| D469,537 S | 1/2003 | Huffman |
| 6,511,318 B2 | 1/2003 | Kim |
| D481,797 S | 11/2003 | Huffman |
| 6,726,477 B2 | 4/2004 | Gittleman |
| D491,269 S | 6/2004 | Tucker et al. |
| 6,869,281 B2 | 3/2005 | Doviack |
| 6,884,068 B2 | 4/2005 | Huffman |
| 6,886,566 B2 | 5/2005 | Eubank |
| 6,932,608 B1 | 8/2005 | Gagliano et al. |
| 6,948,932 B2 | 9/2005 | Jung et al. |
| D512,148 S | 11/2005 | Kwok |
| 7,044,734 B2 | 5/2006 | Huffman |
| D529,177 S | 9/2006 | Huffman |
| D529,178 S | 9/2006 | Huffman |
| 7,108,507 B2 | 9/2006 | Huffman |
| D530,014 S | 10/2006 | Huffman |
| 7,147,465 B2 | 12/2006 | Jung et al. |
| 7,156,660 B2 | 1/2007 | Huffman |
| D537,987 S | 3/2007 | Manzo et al. |
| D539,429 S | 3/2007 | Wong |
| 7,192,277 B2 | 3/2007 | Garland |
| 7,210,931 B1 | 5/2007 | Huffman |
| D547,452 S | 7/2007 | Costello |
| D551,767 S | 9/2007 | Costello |
| 7,303,393 B2 | 12/2007 | Gambacorta |
| D559,986 S | 1/2008 | Huffman et al. |
| 7,338,283 B2 | 3/2008 | Honstein et al. |
| 7,341,451 B2 | 3/2008 | Huffman |
| 7,347,689 B2 | 3/2008 | Huffman |
| D566,281 S | 4/2008 | Huffman |
| D567,378 S | 4/2008 | Nordahl et al. |
| D567,380 S | 4/2008 | Huffman |
| D571,919 S | 6/2008 | Kwon et al. |

OTHER PUBLICATIONS

U.S. Appl. No. 29/216,697, filed Nov. 5, 2004.

* cited by examiner

DENTAL ARTICULATOR

BACKGROUND

1. Technical Field

The invention relates to dental models and methods of forming dental models. More particularly, the invention relates to dental articulators and methods of using the same to form dental models.

2. Related Art

Creating a dental model from a mold of a person's teeth is a well-known practice. Dental models are used for dental work such as, for example, crowns, bridges, and orthodontics. A mold of a person's teeth is typically formed when a patient bites into a pliant casting material that cures to create a mold cavity defining a negative impression of the person's teeth and gums. The mold can represent all or any portion of the person's teeth and gum line. When forming a dental model, a castable material is poured into the negative impression of the mold and the cured castable material results in a stone replica or dental model of the patient's teeth and gums.

One type of dental mold that is becoming increasingly popular is a triple tray mold. Triple tray molds include an impression of opposing top and bottom teeth in a person's mouth. Triple tray molds are most often used to create simultaneously a dental model of a damaged tooth on either the top or bottom of a person's mouth and an opposing dental model of teeth facing the damaged tooth. Triple tray molds can be quadrant shaped representing one or the other side of a person's posterior teeth, or a full arc shape capturing the anterior teeth. Triple tray molds pose problems of proper alignment of teeth impressions of the mold with mounting features of the dental model bases that support the dental model.

In many instances, it is advantageous to mount the dental model to an articulator device that orients cast dental models relative to each other thereby representing a patient's upper and lower teeth positioned relative to each other. Improvements in dental articulators and methods of forming dental models, in particular using triple tray molds, would be advantageous.

SUMMARY

The present disclosure is applicable to dental modeling systems that include, for example, articulators with integrated opposing bases and dental model bases. The present disclosure also relates to pin locators for alignment of teeth of a dental mold with corresponding removable pins of the dental model base. The dental model base can include a plurality of removable pins and indexing protrusions. The pin locator can also include removable and fixed pins for alignment with different teeth of the dental mold. These dental modeling systems and articulators can be designed specifically for modeling anterior and posterior teeth using full arc and quadrant dental molds.

Another aspect of the present disclosure relates to the hinge structure of the articulator. The hinge structure includes connecting arms integrally formed with and extending from each component of the dental modeling system (e.g., upper and lower opposing bases, dental model bases, and pin locators). The hinge structure can include a stop member that restricts relative rotation between two components coupled together in at least one rotation direction. The hinge can have a width that is no greater than a width of at least one of the opposing base and dental model base.

The above summary of the present invention is not intended to describe each embodiment or every implementation of the present invention. The Figures and the detailed description that follow more particularly exemplify a preferred embodiment.

BRIEF DESCRIPTION OF THE DRAWINGS

The invention can be more completely understood in consideration of the following detailed description of preferred embodiments of the invention in connection with the accompanying drawings, in which.

Figure 1:
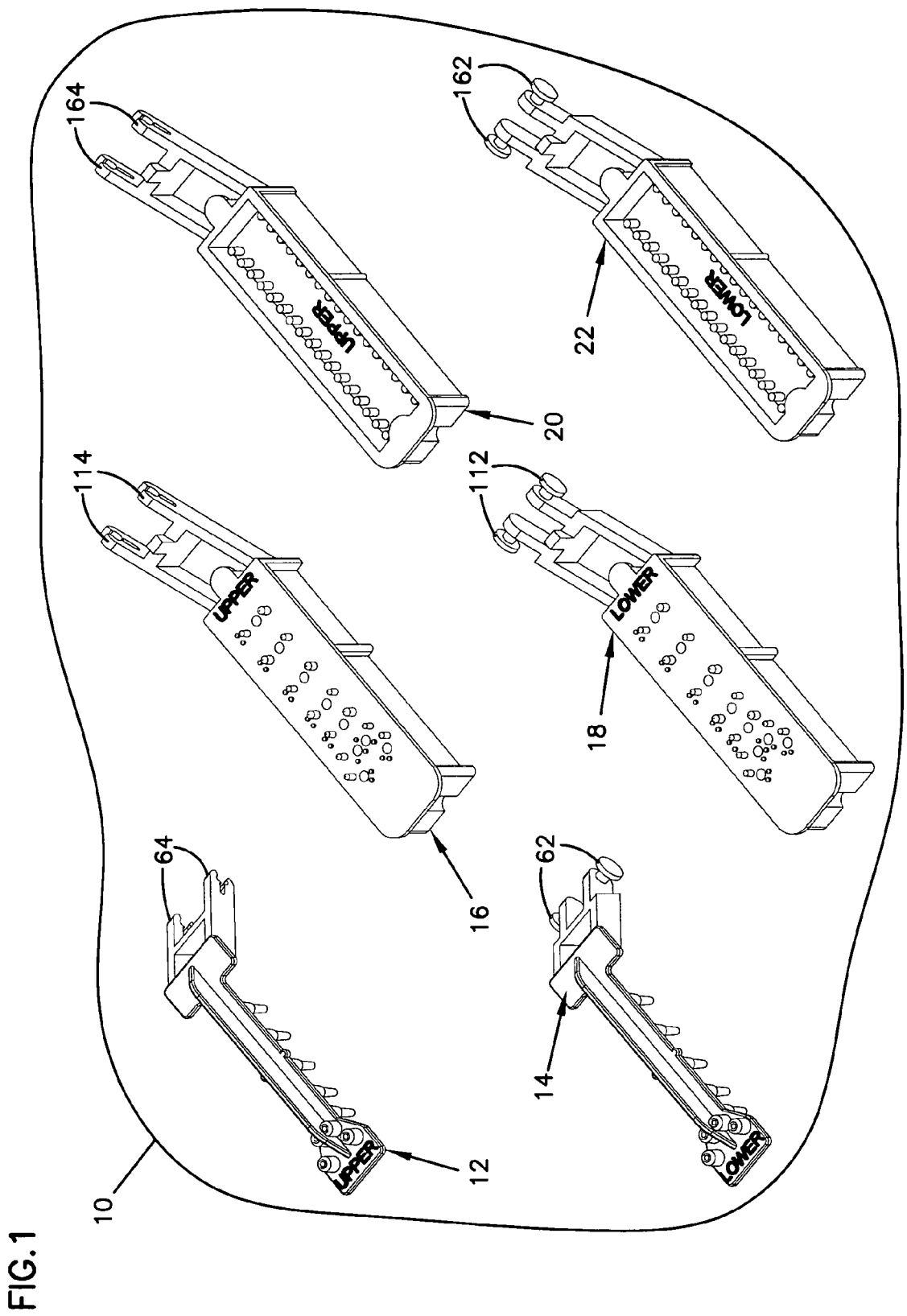
FIG. 1 is a perspective view of an example dental articulator system comprising quadrant versions of upper and lower pin locators, dental model bases, and opposing bases.

While the invention is amenable to various modifications and alternative forms, the specifics thereof have been shown by way of example in the drawings and will be described in detail. It should be understood, however, that the intention is not to limit the invention to the particular embodiment described. On the contrary, the intention is to cover all modifications, equivalents, and alternatives falling with in the spirit and scope of the invention.

DETAILED DESCRIPTION

The present disclosure is applicable to dental modeling systems that include, for example, articulators with integrated opposing bases and dental model bases. The present disclosure also relates to pin locators for improved alignment of teeth of a dental mold when forming a dental model from the mold. The pin locator can include removable pins for use when aligning with different teeth of the dental mold. The dental model base can include a plurality of removable pins and indexing protrusions useful when separating individual teeth from the dental model mounted to the dental model base. The dental modeling systems and articulators described herein can be designed for modeling anterior and posterior teeth using molds that represent primarily anterior or posterior teeth. While the present disclosure should not be so limited, an appreciation of various aspects of the present disclosure will be gained through a discussion of the examples provided below.

I. THE QUADRANT ARTICULATOR SYSTEM OF FIGS. 1-15

Referring to FIGS. 1-15, an example quadrant dental modeling assembly 10 is shown and described. FIG. 1 illustrates the six main components of the system 10 including upper and lower pin locators 12, 14, upper and lower dental bases 16, 18, and upper and lower opposing bases 20, 22. While the upper and lower versions of each of the pin locators, dental model bases, and opposing bases appear in FIG. 1 to have generally the same size, shape, and features, there are some variations between each of the pairs of upper and lower parts. The hinge features of the upper and lower parts are one of the primary differences between the upper and lower parts.

The upper and lower pin locators 12, 14 include features similar to the pin locators described in U.S. Published Patent Application No. 2004/0029071, titled DENTAL MODEL POURING JIG, now U.S. Pat. No. 7,108,507, issued Sep. 26, 2006. The dental bases 16, 18 include features similar to those disclosed in U.S. patent application Ser. No. 29/216,697, titled DENTAL MODEL BASE WITH A PLURALITY OF INDEXING PINS, now U.S. Pat. No. D529,177, issued Sep. 26, 2006. The opposing bases 20, 22 include some features similar to the opposing base disclosed in U.S. Published Patent Application No. 2006/0281043, titled DENTAL MODELING ASSEMBLY AND METHODS, and U.S. application Ser. No. 29/230,408, titled OPPOSING DENTAL MODEL BASE QUADRANT, now U.S. Pat. No. D529,614, issued Oct. 3, 2006. The patent related documents referenced in this paragraph are incorporated herein by reference in their entirety.

A. Pin Locators

The upper and lower pin locators 12, 14 are described with reference to FIGS. 1-5. Each of the pin locators 12, 14 includes a base member 30, a plurality of locator pins 32, a plurality of holes 34 sized to receive tapered pins, and a hinge portion 36. The base member 30 includes top and bottom sides 38, 40, front and rear ends 42, 44, and first and second sides 44, 48. A rib member 50 extends along a longitudinal length of the pin locators. A notch 52 is formed along each of the first and second sides 46, 48 and a molar marker 54 is positioned within the notches 52 for alignment of a first molar (M1 shown in FIGS. 2 and 4B) in a mold of a person's teeth.

The rib 50 can provide additional strength and rigidity for the relatively thin and narrow pin locator shape resulting from the notches 52. The rib 50 can also be used for grasping the pin locators 12, 14. Some advantages of the relatively small size and shape of the pin locators 12, 14 include, for example, the use of minimal amounts of material resulting in reduced cost and improved viewing of the pins from different angles. The design of the pin locators 12, 14 can also result in improved rigidity and strength that provide more accurate positioning of the plurality of locator pins 32.

The bottom side 40 of the pin locators defines a mounting surface (referred to as reference no. 40) to which the locator pins 32 are mounted. The locator pins 32 are spaced apart axially along the length of the pin locators 12, 14 in accordance with the layout of holes shown in FIGS. 14 and 15 as described in further detail below. The pins 32 shown in FIGS. 1-5 correspond to positioning of molars M1-M3 and bicuspids B1-B2 from a mold of a person's teeth. The pins 32 can be removable pins that mount within holes defined in the bottom side 40. Alternatively, the pins 32 can be formed integrally with the bottom side 40.

Figure 13:
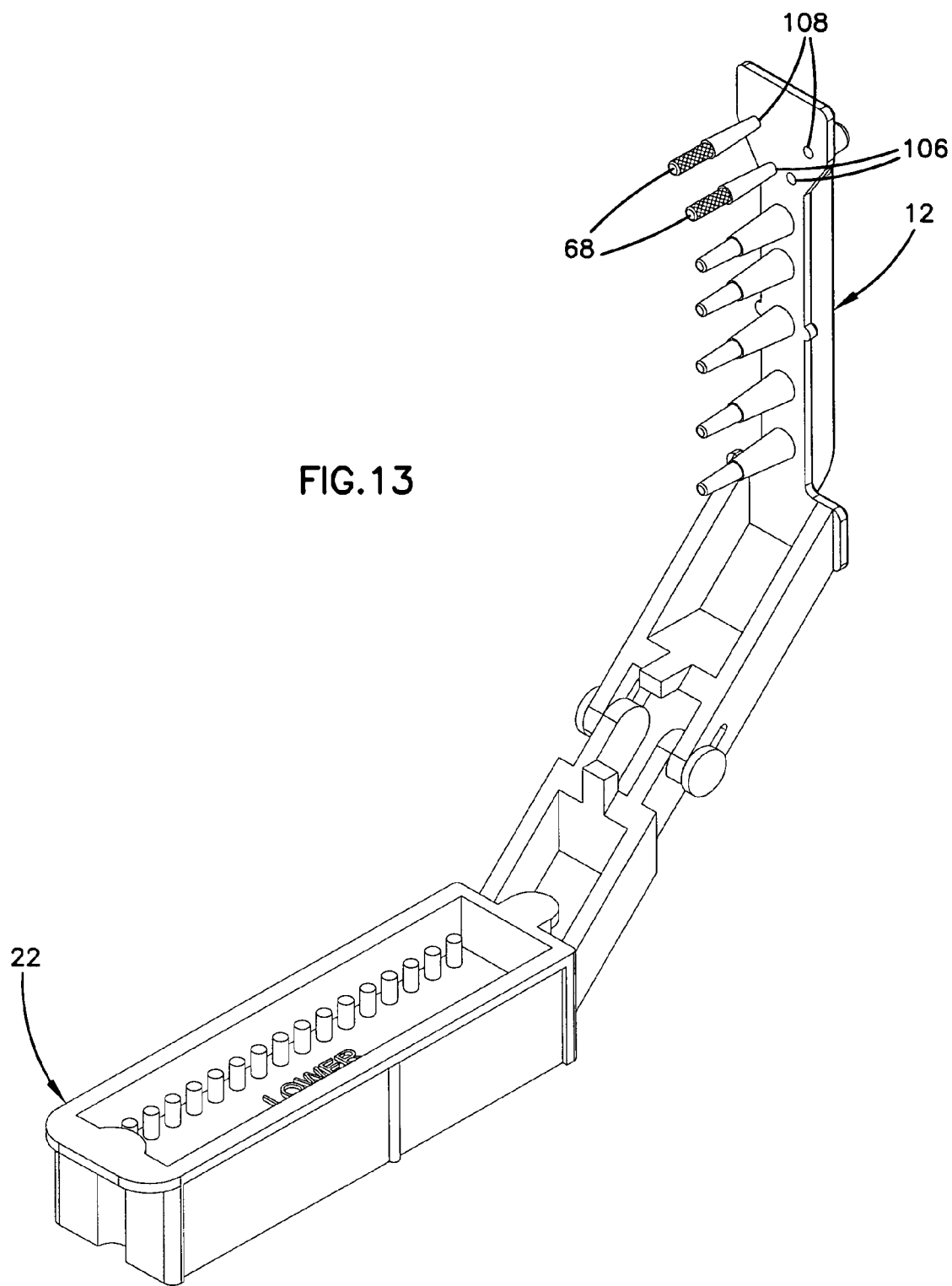
FIG. 13 illustrate a pin layout for the dental model bases shown in FIG. 1 relative to pin layouts for a full arc dental model base.

The plurality of holes 34 extend through the bottom side 40 and are sized to receive removable tapered pins such as pins 68 shown in FIG. 13. The holes 34 are divided into pairs of holes 56, 58 representing positions of cuspid and lateral teeth (see FIG. 2). The pairs of holes 56, 58 are offset from the linear array of locator pins 32. The positioning of holes 56, 58 is also determined in part from the diagram of holes shown in FIGS. 14 and 15.

Another way of defining the holes 34 is to divide them into pairs of holes 57, 59 each positioned on an opposite side of the center line defined by the linear array of locator pins 32. Pairs of holes 57, 59 can include at least one hole of each of the sets of holes 56, 58, thereby including a single cuspid and a single lateral tooth hole. Described in this manner, each of the pairs of holes on opposite sides of the center line represent the curvature of teeth on a right or left side of a person's upper or lower set of teeth. As a result, the pin locators 12, 14 can be used with a mold or impression of a person's left or right side quadrant of teeth. The left and right side pairs 57, 59 each include one of the holes 56, 58 that when aligned with each other have a centerline that intersects at an angle θ (see FIG. 3) relative to the centerline of the pins 32.

The holes 34 can be replaced with locator pins that are removably mounted to the pin locators 12, 14. Alternatively, the locator pins, once positioned within the holes 34, are permanently fixed in place. In other arrangements, one or more of the holes 34 are replaced with permanently mounted locator pins 32.

The hinge portion 36 of each of the pin locators 12, 14 includes a connecting arm 60, a male or female hinge connector for the lower and upper pin locators 12, 14, respectively, and a stop member 66. At least a portion of connecting arm 60 extends at an angle β (see FIG. 4A) relative to a plane of the mounting surface and bottom side 40. The connecting arm can include a plurality of leg or arm members that extend from the base member 30. The embodiment of FIGS. 1-5 includes connecting arm features that are coupled at a first end to the bottom side 40 of the base member and are coupled at a second end to the male or female hinge connector 62, 64.

The stop member 66 extends from the connecting arm in a direction generally perpendicular to the mounting surface defined at the bottom side 40. The stop member 66 is positioned along the length of the connecting arm between the attachment point with base member 30 and the male or female connectors 62, 64. In other embodiments, the stop member 66 can extend at other angles other than the generally perpendicular direction relative to bottom side surface 40 shown in the Figures. Further, the stop member 66 can have different shapes and sizes in other embodiments and contact other features of the opposing system component (e.g., dental model base and opposing base) besides the similar shaped and oriented stop members 116 and 166 described below.

B. Dental Model Bases

The dental model bases 16, 18 each include a base member 70, a plurality of holes 72 including a linear array of unequally spaced holes 73 and cuspid and lateral teeth holes 106, 108. The bases 16, 18 also include a plurality of large, medium and small indexing members 73-75, and a hinge portion 76.

The base member 70 includes top and bottom sides 78, 80 wherein the bottom side defines a primary mounting surface (referred to as reference no. 80) for mounting a dental model. The base member 70 also includes front and rear ends 82, 84, first and second sides 86, 88, a continuous sidewall 90 defining a cavity 92 (see FIG. 8) wherein a plurality of protrusions 100 are positioned. The base member 70 also includes spacer rod recesses 96, 98 formed in the front and rear ends 82, 84 and punch-outs 97 in alignment with the recesses 96, 98 through which spacer rods can extend (see FIGS. 11 and 12). Molar markers 92 are positioned on the first and second sides 86, 88 for alignment of a first molar (M1) of a dental mold with one of the holes 72 associated with the first molar (M1) of a resulting dental model.

The dental model bases 16, 18 are designed to use a minimum amount of material in the construction thereof while still providing the desired structural rigidity for supporting the plurality of tapered pins 115 and a dental model mounted to the bottom side 80. One way in which the amount of material used in the dental model base is minimized is to form the bases 16, 18 with cavity 92 defined by the continuous sidewall 90. The plurality protrusions 100 are aligned with one of the plurality of holes 72 to provide a support structure for retaining the plurality of tapered pins 115. The holes 72 and protrusions 100 define an interior cavity that is tapered at an angle that matches the tapered surface of the pins 115 thereby providing an interference fit between the tapered pins and the internal tapered cavity. Alternatively, the holes 72 do not include a tapered interior cavity. In other arrangements, the holes 72 include an internal tapered cavity and the pins 115 do not include a tapered surface. The holes 72 can be configured to permanently mount or removably mount the pins 115 to the bases 16, 18.

The holes 72 are positioned along the bottom side 80 with a spacing that matches an average position of actual teeth in a person's mouth. Example hole spacings are described with reference to FIGS. 14 and 15. In alternative arrangements, the holes 72 can having different spacings and multiple rows of holes, such as the holes described in U.S. Pat. Nos. 6,471,513 and D452,321, which are incorporated herein by reference. Alternatively, the holes 72 can be drilled into bottom side 80 after determining an exact position of the hole relative to a tooth of interest in the dental mold as described in U.S. Pat. No. 6,884,068, which is incorporated herein by reference.

The large and medium indexing members 73, 74 are positioned on alternating sides of each of the linear array of holes 73 on the primary surface 80. The small indexing members 74 are shown positioned along one lateral side of the holes 72. The combination of large, medium and small indexing members 73-75 help to ensure unintentional misplacement of individual teeth of the resulting dental on the dental model bases 16, 18. Typically, after the dental model is formed (e.g., see dental models 6, 8 in FIGS. 9 and 10) the dental models are cut into one or more teeth with at least the tooth of interest being separated from portions of the dental model and opposing sides of that tooth. In many cases, multiple teeth are cut from a single model. Removing and replacing those cut out teeth with respect to the dental model bases 16, 18 can result in misplacement of those teeth. The indexing members 73-75, due to their differing sizes and positions can inhibit flush mounting of a tooth model relative to the primary surface 80 if the tapered pin associated with that tooth model is inserted into an incorrect hole.

While the indexing members 73-75 are shown in a specific arrangement having specific sizes in the Figures, this shape, size and orientation of indexing members is merely exemplary of many different possible shapes, sizes and orientations. For example, in other embodiments different combinations of small, medium and large, small and medium, small and large, or medium and large indexing members can be used in association with one or more of the holes 72. Furthermore, the shape of the indexing members can differ from the generally cylindrical, peg-shaped indexing members shown in the figures. In other embodiments, the indexing members can have rectangular, triangular or other shaped cross-sections. Alternatively, one or more of the indexing members 73-75 is not used with the bases 16, 18. Some configurations of bases 16, 18 can include different features that provide indexing functions. In one example, the holes 72 have different sizes for different sized pins 115.

Figure 7:
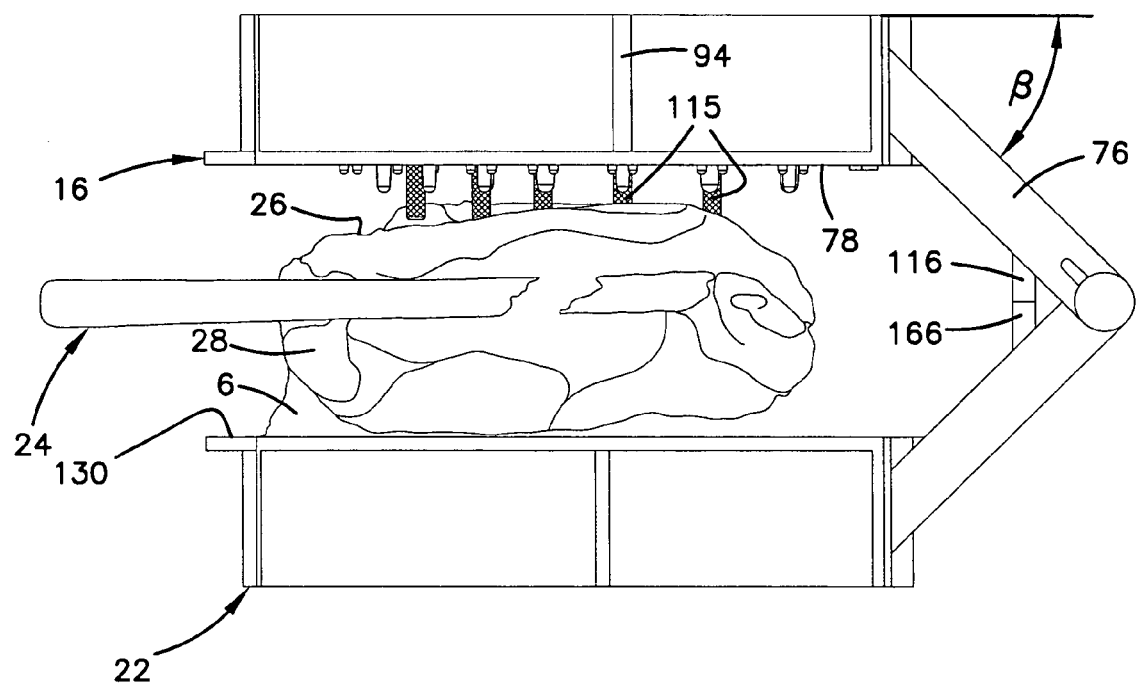
FIG. 7 is a side view of the arrangement of FIG. 6 with removable pins of the upper dental model base in alignment with teeth impressions of the dental mold.

The hinge portion 76 includes connecting arm 110, male and female hinge connectors 112, 114 associated with the lower and upper dental model bases 16, 18, respectively, and a stop member 116. The hinge portions 76 are configured substantially similar to the hinge portions 36 of the upper and lower pin locators 12, 14. The connecting arm 110 is coupled at one end to the rear end 84 of the base member 70, and coupled at an opposing end to the male or female hinge connector 112, 114. The connecting arm can include separate legs or arms. The connecting arm 110 extends from the base member 70 at an angle β as shown in FIG. 7.

The stop member 116 is positioned between legs of the connecting arm and is configured to engage a stop member of the pin locator, dental model base, or opposing base to which the dental model bases 16, 18 are coupled via the hinge connection of the hinge connector 112, 114. The stop member 116 extends in a generally perpendicular direction relative to the surface 80. In other embodiments, the stop member 116 can extend at other angles other than the generally perpendicular direction. Further, the stop member 116 can have different shapes and sizes in other embodiments and contact other features of the opposing system component (e.g., pin locator, opposing base, or another dental model base) besides the similar shaped and oriented stop members 66 and 166 described herein. The connecting arm extends from a rear surface of the base member 70, but can extend from other surfaces, such as surface 80, in other embodiments.

A pair of stop rods 118, 119 can be coupled to the base member 70 in the recesses 96, 98 at front and rear ends 82, 84 of the base member 70. The rods can extend through the punch out 97 in the bottom side 80 (see FIGS. 11 and 12). The stop rods can be used in addition to or in place of the stop member 116 to ensure a predetermined relative position of the base member 70 relative to the opposing bases 20, 22 or a pin locator base member 30 to which the bases 16, 18 are attached.

C. Opposing Bases

Figure 3:
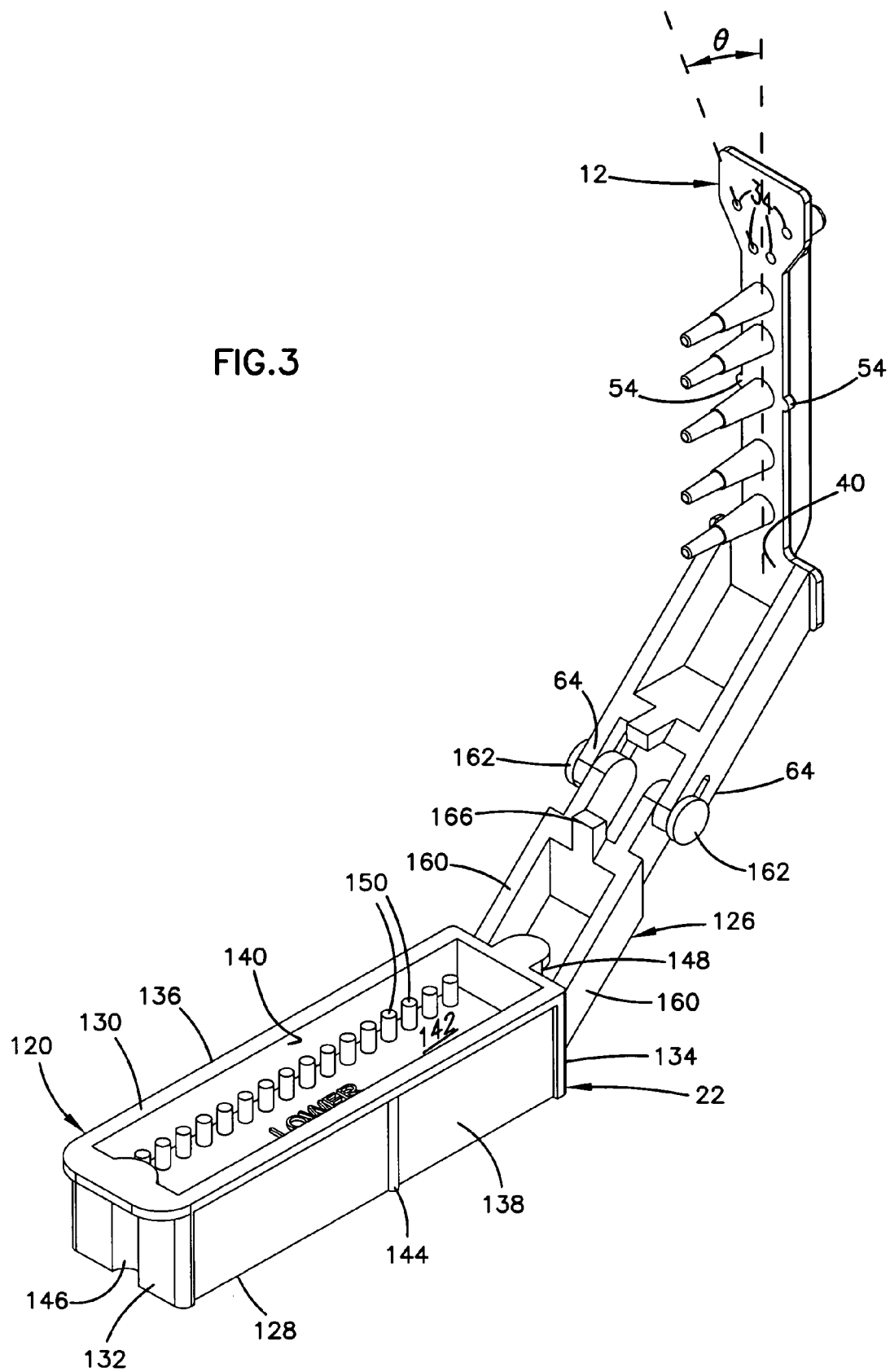
FIG. 3 is a perspective view showing the upper pin locator of FIG. 2 coupled to a lower opposing base with a hinged connection.

The opposing bases 20, 22 are illustrated with reference to FIGS. 3, 4A and 4B. The opposing bases 20, 22 each include a base member 120 and a hinge portion 126. The base member 120 includes top and bottom sides 128, 130. The bottom side 130 defines a mounting or engagement surface (also identified with reference no. 130) that supports an opposing dental model. The base member 120 includes front and rear ends 132, 134, first and second sides 136, 138, a recessed floor 142 defined by a continuous sidewall 140, and a plurality of engagement pins 150 extending from the recessed floor 142 adjacent to an interior side of the continuous sidewall 140. The recessed floor 142 can be positioned at any location between the top and bottom sides 128, 130. Preferably, the recessed floor 142 is positioned about one half the distance H defined between the sides 128, 130 (see FIG. 4A). By positioning the recessed floor 142 at a location between the sides 128, 130, the amount of stone required to generate the opposing dental model can be minimized while still providing sufficient depth to retain the opposing dental model in the opposing base.

The engagement pins 150 can have different configurations and arrangements in other embodiments. For example, the engagement pins can be even distributed across the recessed floor 142 rather than positioned along the side edge of the floor 142 adjacent to the continuous side wall 140. Further, the engagement pins can have different shapes rather than the circular cross-sectioned cylindrical peg shape shown in the Figures.

The opposing bases can also include spacer rod contacts 146, 148 positioned at opposing first and second ends 132, 134. The spacer rod contacts 146, 148 are sized and positioned to engage the stop rods 118, 119 mounted to the dental model base 16, 18 when the dental model base is coupled with a hinge connection to the opposing base (see FIG. 12).

The opposing bases 120, 122 also include molar markers 144 positioned along the sides 136, 138 in alignment with a typical position of the first molar M1 of a dental mold. The molar marker 144 can be useful for aligning the dental mold axially along the length of the opposing base during the process of making a dental model using the dental modeling assembly 10.

The stop member 166 is positioned between legs of the connecting arm 110 and is configured to engage a stop member of the pin locator or dental model base to which the opposing bases 20, 22 are coupled via the hinge connection of the hinge connector 162, 164. The stop member 166 extends in a generally perpendicular direction relative to the surface 130. In other embodiments, the stop member 166 can extend at other angles other than the generally perpendicular direction. Further, the stop member 166 can have different shapes and sizes in other embodiments and contact other features of the opposing system component (e.g., pin locator or dental model base) besides the similar shaped and oriented stop members 66 and 116 described herein. The connecting arm extends from a rear surface of the base member 120, but can extend from other surfaces, such as surface 130, in other embodiments.

D. Dental Mold

Figure 2:
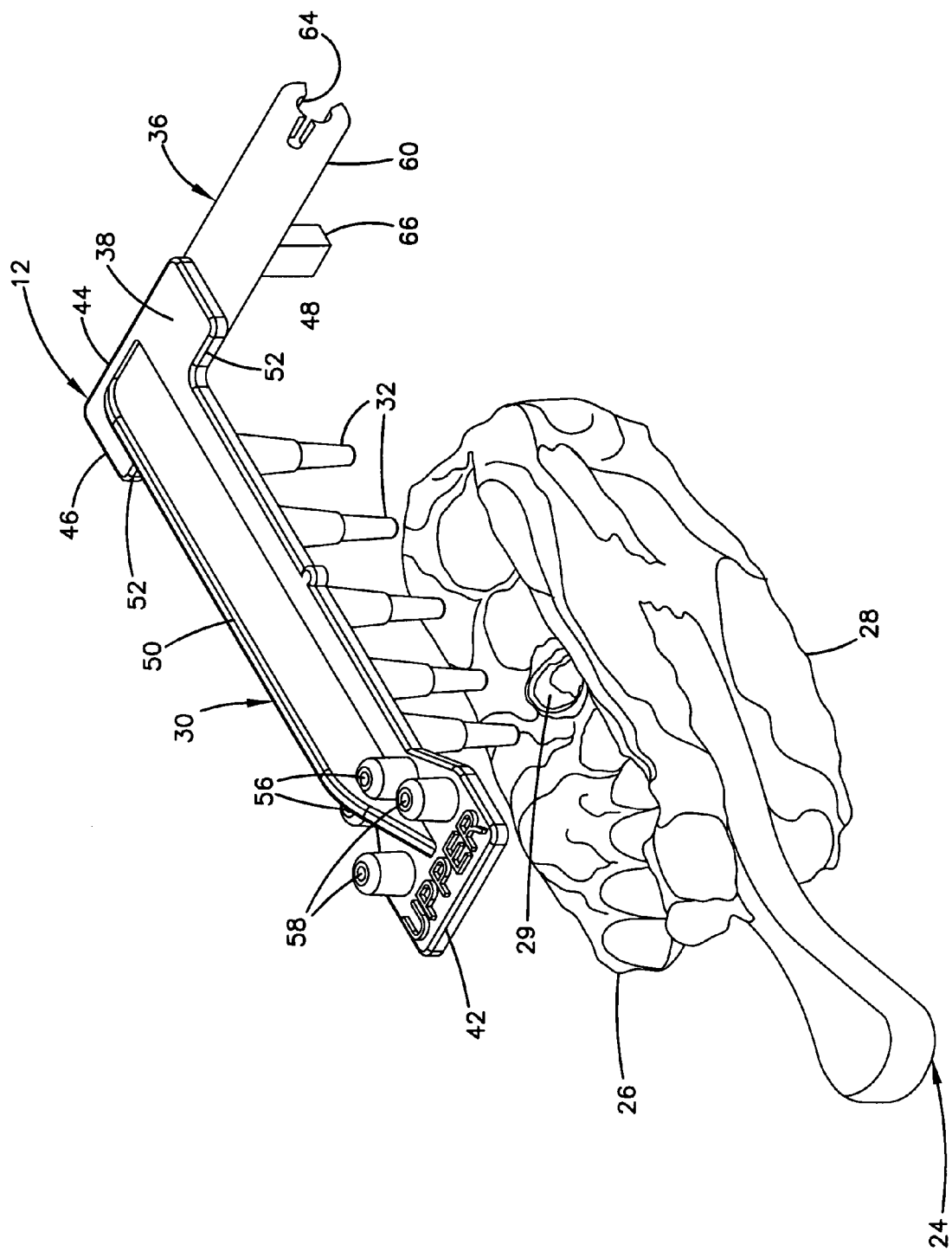
FIG. 2 is a perspective view of the upper pin locator shown in FIG. 1 in alignment with teeth impressions of a dental mold.
Figure 4A:
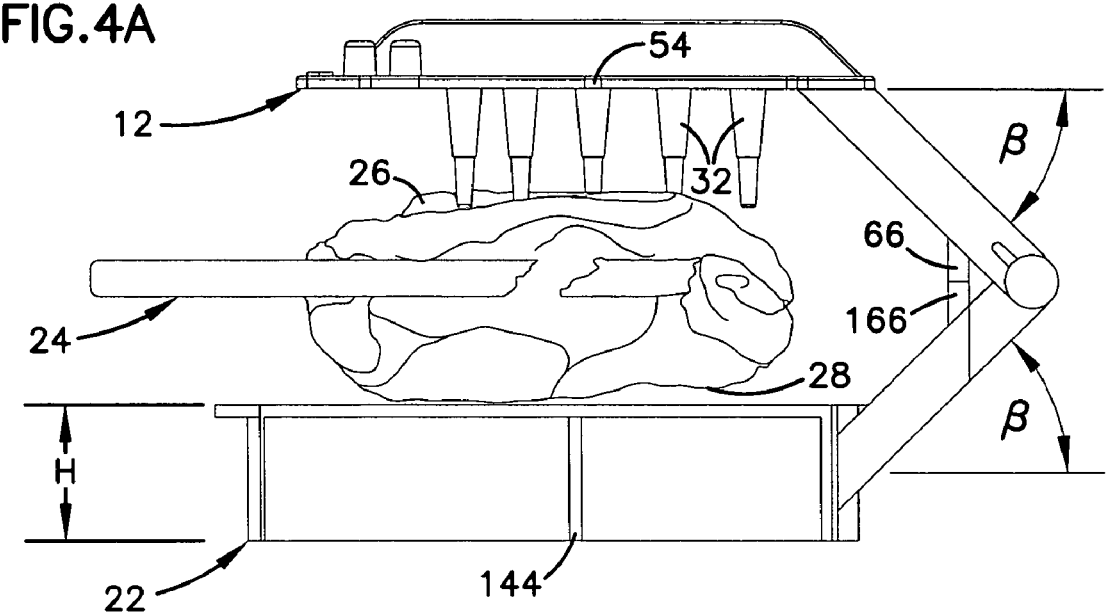
FIG. 4A is a side view and FIG. 4B is a perspective view showing the dental mold of FIG. 2 oriented between the lower opposing base and upper pin locator shown in FIG. 3.
Figure 4B:
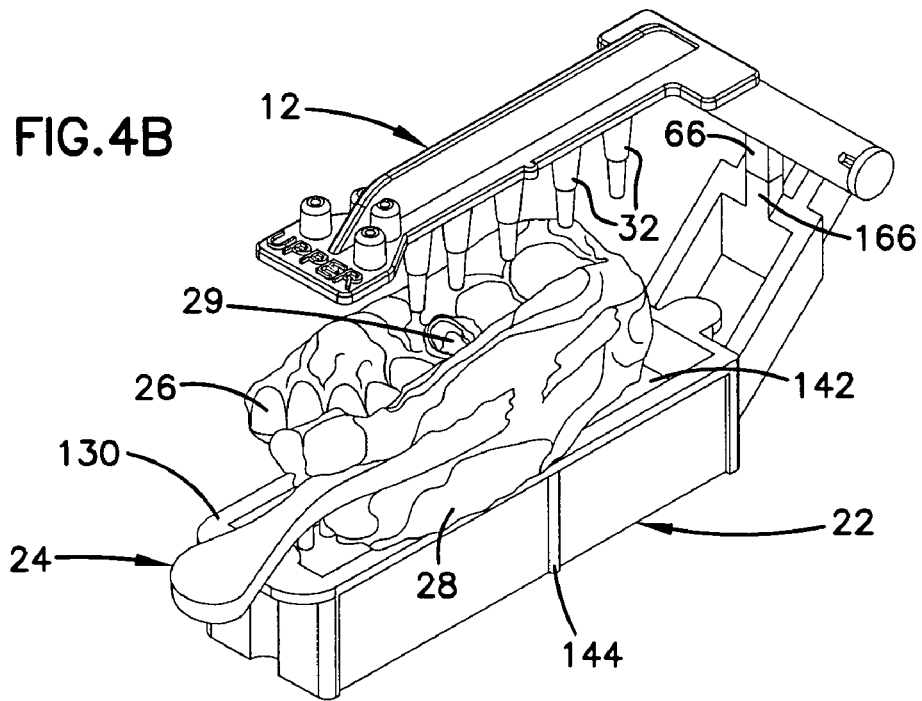

Referring to FIGS. 2, and 4A-B, an example dental mold 24 is shown. The mold 24 has upper and lower side impressions 26, 28 that are impressions of a person's opposed upper and lower teeth on a person's left side of the mouth. The mold 24 includes an impression 29 of a damaged tooth of interest. That is the second bicuspid (B2 shown in FIGS. 14 and 15) tooth. The mold 24 is well known in the art as a triple tray mold, and more specifically a quadrant triple tray mold. A quadrant mold is distinguished from a full arc mold in that the quadrant captures the teeth impression of only a portion of the person's full arc of teeth. A dental modeling assembly for a full arc mold is described in detail with reference to FIGS. 16-21.

E. Dental Modeling Methods

A method of creating a dental model using the dental modeling assembly 10 is now described with reference to FIGS. 1-15. First with reference to FIG. 2, the dental mold 24 is held with a side of the mold including the tooth of interest 29 visible and accessible for alignment of a pin locator over the teeth impressions. In this case, the upper side impression 26 includes the tooth of interest 29 and the upper pin locator 12 is held suspended above the mold 24 with the mold marker 54 in alignment with the first molar impression M1. Because the locator pins 32 of the pin locators 12, 14 can have slightly different spacings therebetween as explained below with reference to the hole layouts of FIGS. 14 and 15, the technician must determine whether the pin locator selected is the most correct one for the size of mold and the side of the mold (upper or lower) having the tooth in question 29.

The dental modeling assembly 10 is described with reference to a single mouth size. In other embodiments, additional dental modeling assembly components can be provided that have different sizes that correspond to, for example, small, medium and large sized mouths. A way in which the different sized mouths are accounted for is discussed below with reference to FIGS. 14 and 15. Therefore, in addition to the step of determining whether the tooth of interest 29 is part of an upper or lower tooth impression, a further step of determining which of a number of different sized upper or lower pin locators is best suited for use with a particular mold 24 can be included.

Once the mold 24 is tested for upper or lower and the size of the appropriate pin locator, the selected pin locator (in this case an upper pin locator 12) is connected to an opposing base of the opposite side (the lower opposing base 22 in this example). The upper pin locator 12 includes female hinge connectors 64 that are sized to engage the male hinge connectors 162 of the opposing base 22, as shown in FIG. 3.

With reference to FIGS. 4A and 4B, the mold 24 is next positioned with the lower side impression 28 facing the bottom side 130 of the opposing base 22 and the upper pin locator 12 is rotated into a closed position with the locator pins 32 facing the teeth impressions on the upper side 26 of the mold 24. The closed position is defined by the stop member 66 engaging the stop member 166 of the opposing base. If rotation into this closed position is obstructed in some way (e.g., due to contact of the pins 32 with excess material on the mold 24) the mold 24 can be trimmed around its peripheral borders as necessary.

It can be advantageous to make a mark on a side surface of the mold 24 in alignment with the first molar M1 so that the technician can more easily align the molar M1 with the molar markers 54 of the pin locator and 144 of the opposing base. Such a mark can be made by the technician using, for example, a permanent marker.

Figure 5:
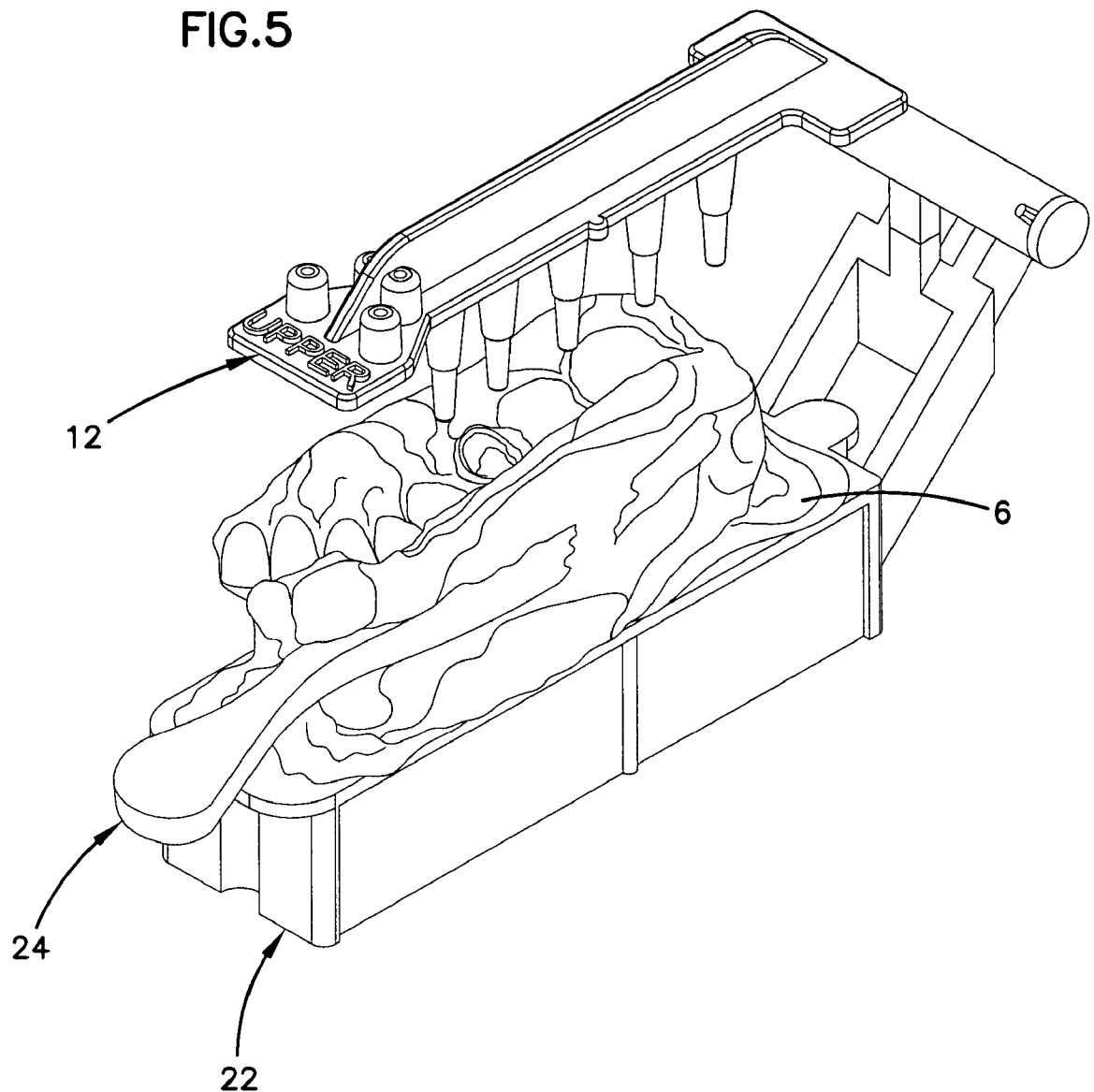
FIG. 5 is a perspective view showing the arrangement of FIG. 4 with one side of the dental mold secured to the lower opposing base with a curable material and pins of the upper pin locator aligned with teeth impressions of an opposite side of the dental mold.

With reference to FIG. 5, the lower side 28 of the mold 24 and the opposing base are filled with a first moldable material. Preferably, most if not all of the recessed floor 142 and engagement pins 150 are covered with the first moldable material. The opposing base is filled with the first moldable material to at least the bottom side 130, if not overflowing from the bottom side 130. The mold 24 is then positioned with the first moldable material in the lower side impression 28 in engagement with the first moldable material in the opposing base 22. The teeth impressions in the upper side impression 26 are then aligned with the locator pins 32. The mold 24 can be vibrated or agitated relative to the opposing base 22 if necessary to provide a proper spacing between the upper side impressions 26 and the locator pins 32. With mold 24 properly aligned relative to the indexing pins 32, the first moldable material is allowed to set to form the first or lower dental model 6.

Figure 6:
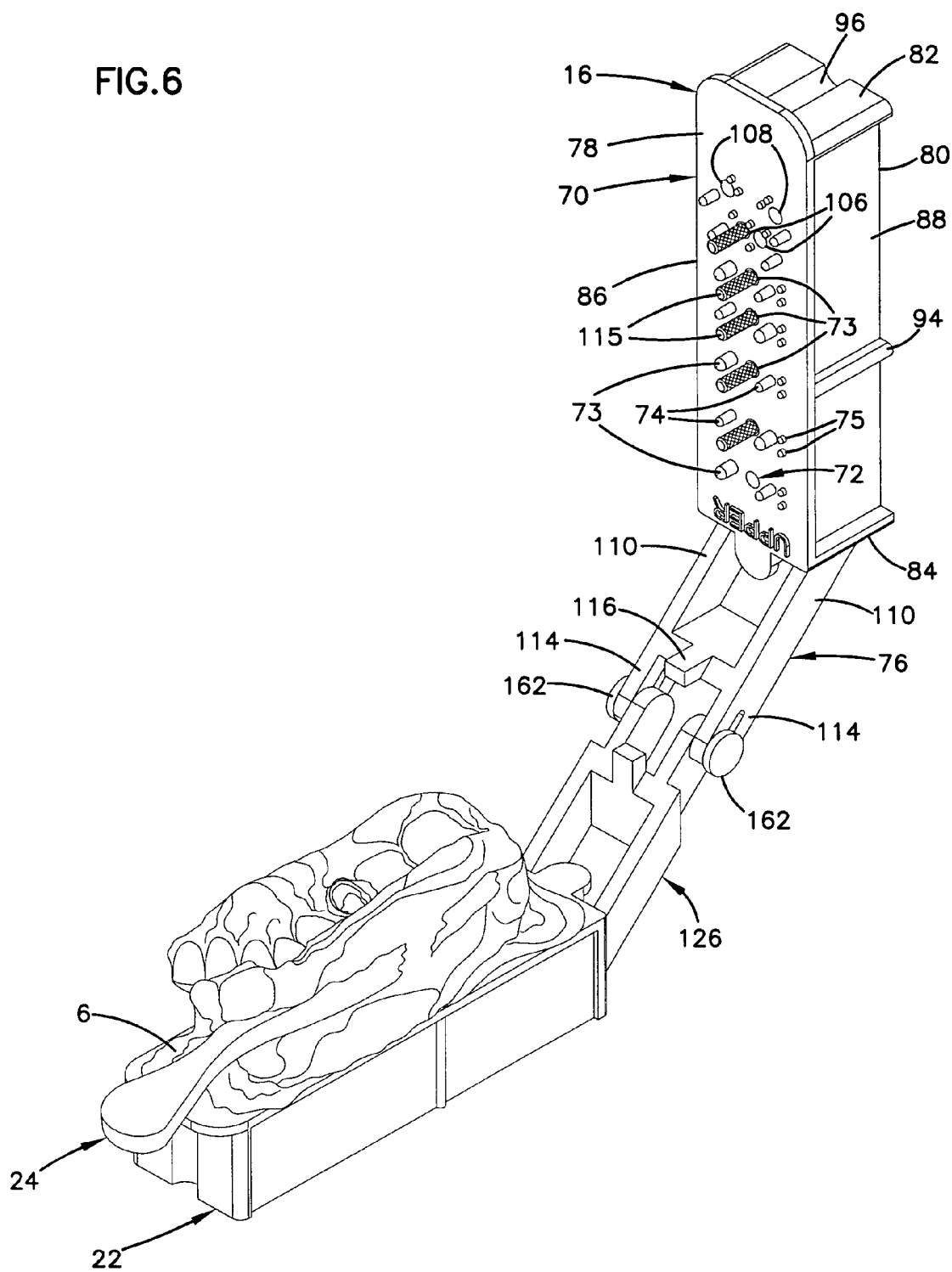
FIG. 6 is a perspective view showing the dental mold and lower opposing base of FIG. 5 and an upper dental model base coupled to the lower opposing base with a hinged connection.

The upper pin locator 12 is replaced with an upper dental model base 16 as shown in FIG. 6. The dental model base 16 is prepared by inserting at least one tapered pin 115 into the hole 72 corresponding to the tooth of interest 29 on the mold 24. As discussed above, the tooth of interest 29 is the second bicuspid tooth. In many cases, it is advantageous to prepare the dental model base 16 for removable mounting of teeth on opposing sides of the tooth in question. For example, additional tapered pins 115 can be inserted into others of the holes 72 including holes 73 of the linear array and at least one of the holes 106 representing the cuspid and lateral teeth impression in the mold 24. The dental model base 16 is then rotated into the closed position until the stop member 116 of base 16 engages the stop 166 of the opposing base 22 as shown in FIG. 7. The technician checks for any interference between the mold 24 and base 16 that may require further trimming of the mold 24 to ensure that the stops 116, 166 engage properly before any portions of the mold 24 engage the features of base 16, including the tapered pins 115.

Figure 8:
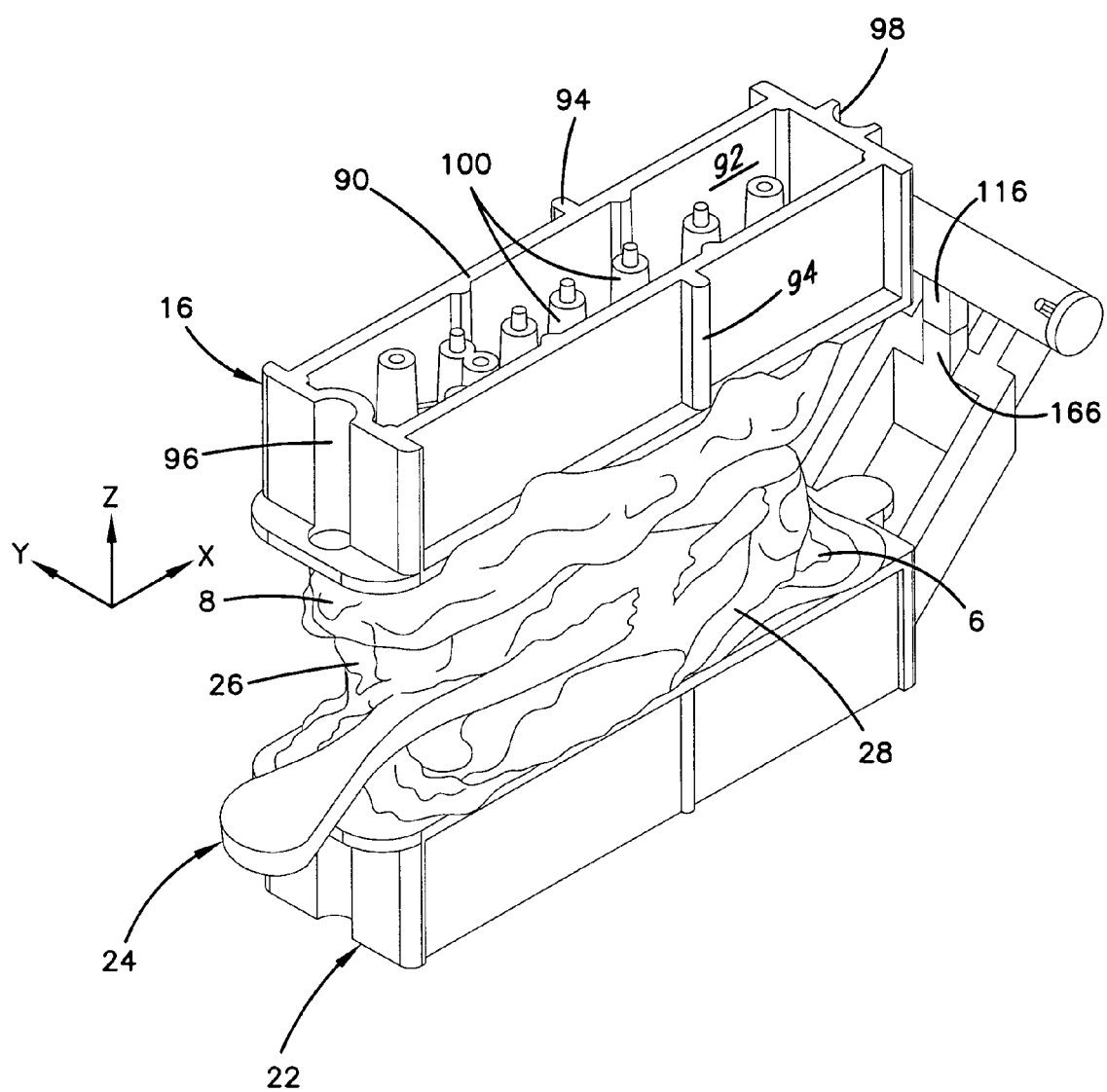
FIG. 8 is a perspective view showing the dental mold secured to the upper dental model base and lower opposing base with curable material.

Referring now to FIG. 8, the dental model base 16 is next rotated into an open position, the upper side impression 26 of the mold 24 is filled with a second moldable material, and the bottom side 80 of the base 16 along with the exposed ends of tapered pins 115 and the indexing members 73-75 are covered with the second moldable material. The base 16 is then rotated towards the closed position until the stop members 116, 166 engage. In order to reach the fully rotated position shown in FIG. 8 with the stop members 116, 166 in engagement, some of the second moldable material can be pressed laterally out between the mold 24 and the base 16. The base 16 can require agitation or vibration relative to the mold 24 in order to ensure the base 16 maintains the closed position with the stops 116, 166 engaged without constant pressure applied to keep the stops 116, 166 in contact. The second moldable material is then allowed to set into stone thereby generating the second or upper dental model 8.

Figure 9:
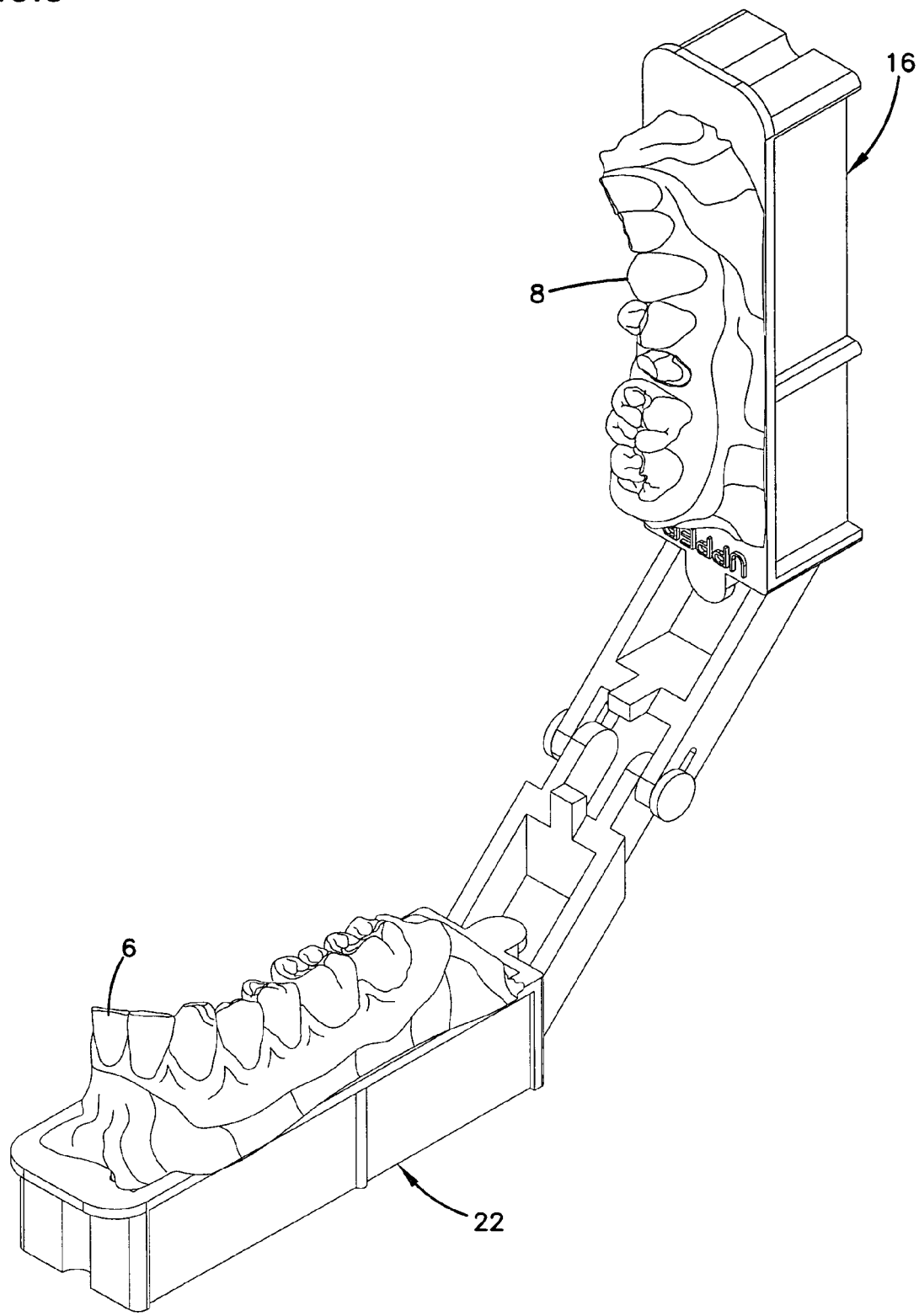
FIG. 9 is a perspective view showing lower and upper dental models coupled to respective lower opposing and upper dental model bases, and the dental mold removed.
Figure 10:
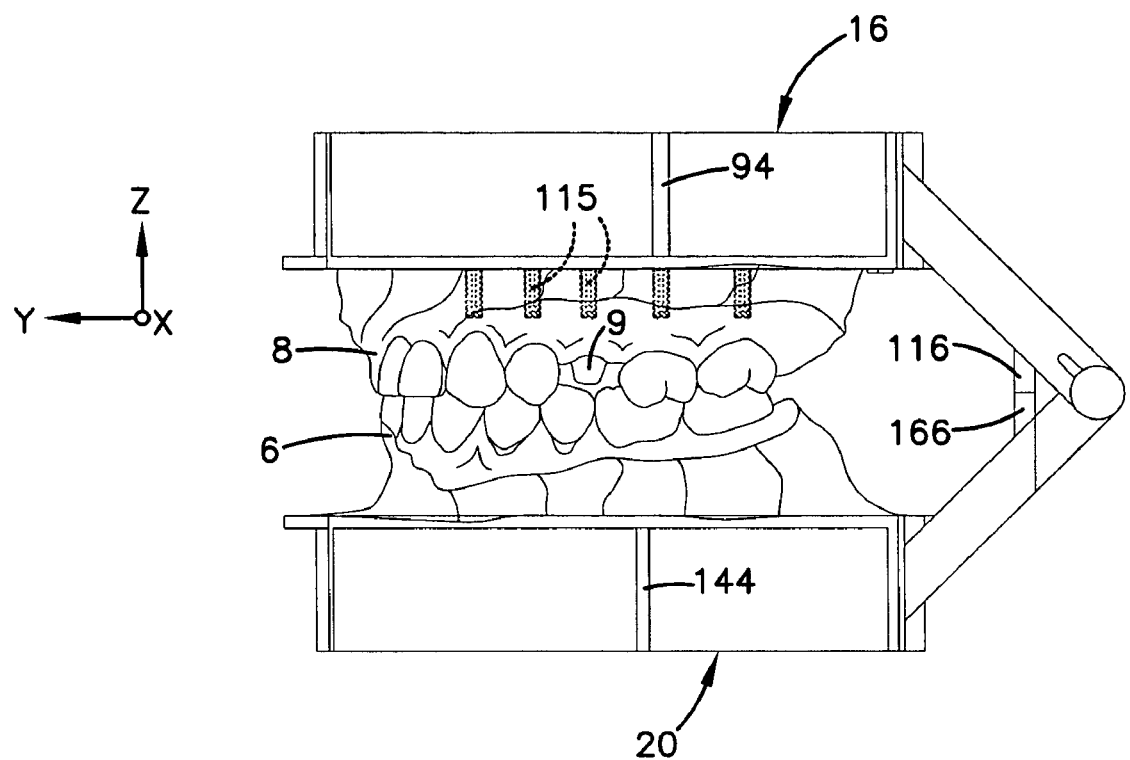
FIG. 10 is a side view of the dental models shown in FIG. 9 with the removable pins shown in broken line to illustrate alignment of the removable pins with teeth of the upper dental model.

After the second moldable material is fully set as model 8, the mold 24 is removed from the models 6, 8 as shown in FIG. 9. The base 16 can be rotated again into the closed position relative to opposing base 22 with the stops 116, 166 in engagement as shown in FIG. 10 where the models 6, 8 can be articulated relative to each other by relative axial and lateral translational movement and rotational movement about the X, Y and Z axis' relative to each other. The models 6, 8 can be articulated due to the inherent flexibility in the structure of the hinge portion 76 of the base 16 and the hinge portion 126 of the base 22.

If the technician would like to remove the resulting model 9 of the tooth of interest from the base 16, the technician can cut through the model 8 on opposing sides of the tooth model 9 in the Z axis direction. Other teeth on opposing sides of the tooth model 9 can also be removed by cutting on opposing sides of each of each tooth that has an associated tapered pin 115. FIG. 10 illustrates the model 8 including tapered pins 115 associated with first and second molars, first and second bicuspids (the second bicuspid represented by tooth model 9), and a cuspid tooth. As discussed above, reinserting the tapered pins 115 into the plurality of holes 72 of the base 16 can be more accurately ensured due to the arrangement and sizes of indexing members 73-75.

The completed models 6, 8 shown in FIGS. 9 and 10 provide a unitary system of dental model bases with dental models with articulator capability. Preferably, no separate and distinct articulator device is required in order to provide the proper relative spacing and arrangement between the models 6, 8 required for articulation. The term articulation is defined as relative movement between upper and lower teeth models, and can include side-to-side and front-to-back translation movement, as well as various rotational movement such as pivoting at a hinge connection between the teeth models. Thus, no additional articulator structure is required to provide some types of articulation in addition to the dental modeling assembly 10 used to generate the models 6, 8 themselves.

Figure 12A:
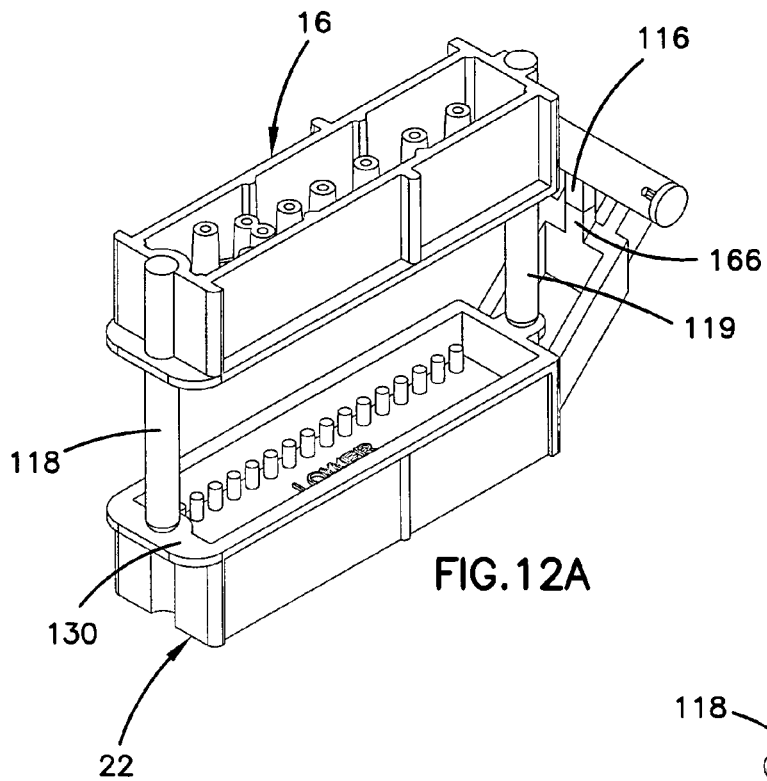
FIG. 12A is a perspective view of the bases shown in FIG. 11 with the stop rods rotated into engagement with the lower opposing base.
Figure 12B:
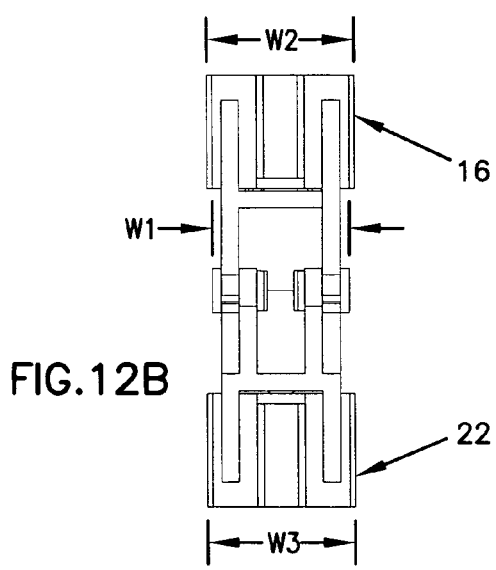
FIG. 12B is a rear view of the bases shown in FIG. 12A.
Figure 11:
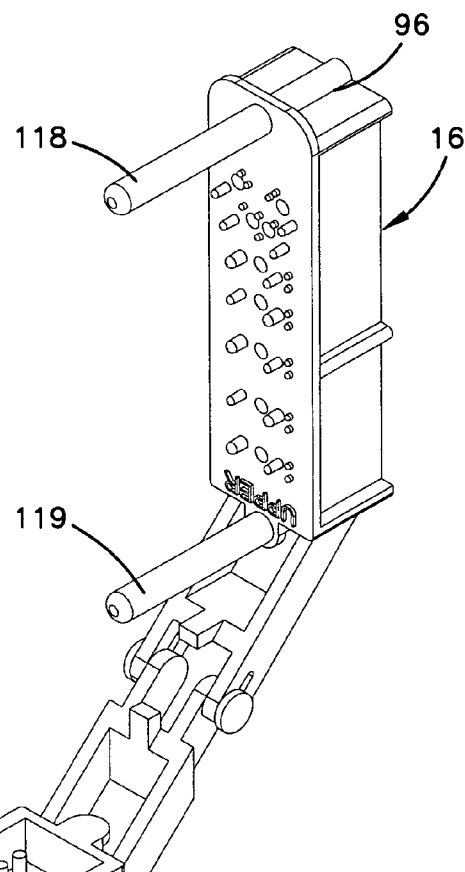
FIG. 11 is a perspective view showing hinged connection of the lower opposing base and upper dental model base, and stop rods coupled at front and rear ends of the dental model base.

One considerations for ensuring correct relative spacing between models 6, 8 is ensuring that the bottom side 80 of the model base 16 and bottom side 130 of the opposing base 22 are parallel to each other when the first and second moldable materials are cured. One way in which this parallel relationship can be more accurately ensured is the addition of stop members 118, 119, which are arranged to engage contacts 146, 148 of opposing base 22. FIGS. 11, 12A and 12B illustrate the markers 118, 119 positioned within the spacer rod recesses 96, 98 and protruding through the punch out 97 on bottom side 80. The rods 118, 119 can be secured in place (e.g., using an adhesive) if added as a separate piece to the base member 16. Alternatively, the rods 118, 119 can be integrally molded as part of the base 70 of the dental model base 16. One or both of the rods 118, 119 can be used in addition to or in place of the engagement of stops 116, 166. A length of the rods 118, 119 can be pre-cut at a certain length that provides a pre-set spacing. For example, one length of rod 118 can provide for an end of the rod 118 to be flush mounted the top surface 78 of the base 16 while an opposing end of the rod 118 engages the opposing base contact 146 to provide parallel alignment of the surface 88 with the surface 130. In other embodiments, the length of rod 118 can provide for the same flush mount with top side 78 while providing a nonparallel arrangement of the surfaces 80, 130.

The components 12, 14, 16, 18, 20, 22 of the dental modeling assembly 10 have an overall width that maintains a consistent form factor. For example, referring to FIG. 12B, the maximum width W1 of hinge portion 76 of the base 16 and hinge portion 126 of opposing base 22 is no greater than a width W2, W3 the base members 70, 120 of bases 16, 22, respectively. This width relationship of hinge portions 76, 126 relative to the base members 70, 120 can provide some advantages. One advantage is that the hinge portions 76, 126 do not obstruct a grinding wheel when grinding excess portions of the first and second models 6, 8 along the sides 86, 88 of base 16 and along sides 136, 138 of base 22. Another advantage relates to the relatively elongate, narrow structure of the hinge portions 76, 126 that can provide a realistic articulation representative of the anatomy of a person's mouth and jaw. In some embodiments, merely changing the thickness of the connecting arm 110, 160 of the hinge portions 76, 126 can be used to fine tune the articulation for different applications. A still further possible advantage of the configuration of hinge portions 76, 126 is that the interface of the male and female portions 114, 162 is focused in the axial direction and lateral directions rather than in some angled direction, which can add to the accuracy of the articulation.

Referring now to FIG. 13, the pin locator 12, 14 can be customized for use in modeling cuspid and lateral teeth associated with left or right sides of a person's mouth using removable pins 68 and the holes 106, 108. Typically, 0-2 pins 68 can be used in any given modeling method using the dental modeling assembly 10. While holes 106, 108 are shown with pin locators 12, 14 in this embodiment, other embodiments can be configured with an additional set of holes corresponding to central teeth of the right and left sides of a person's mouth. In order to provide ample room for positioning of a hole corresponding to a central tooth, the front end 42 of the pin locators 12, 14 would require additional width and length.

Figure 14:
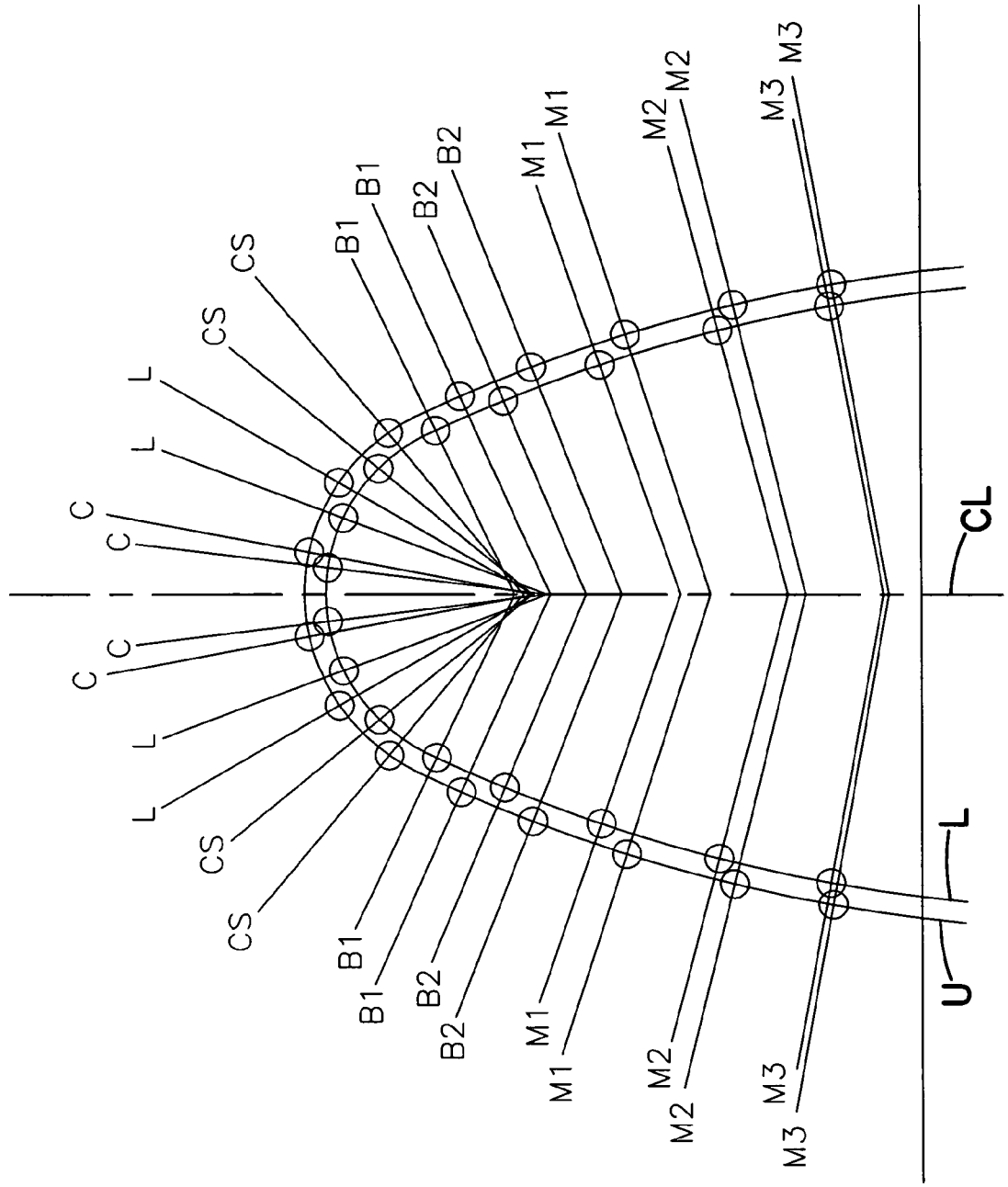
FIG. 14 illustrates a pinhole layout for upper and lower arc tooth locations.
Figure 15:
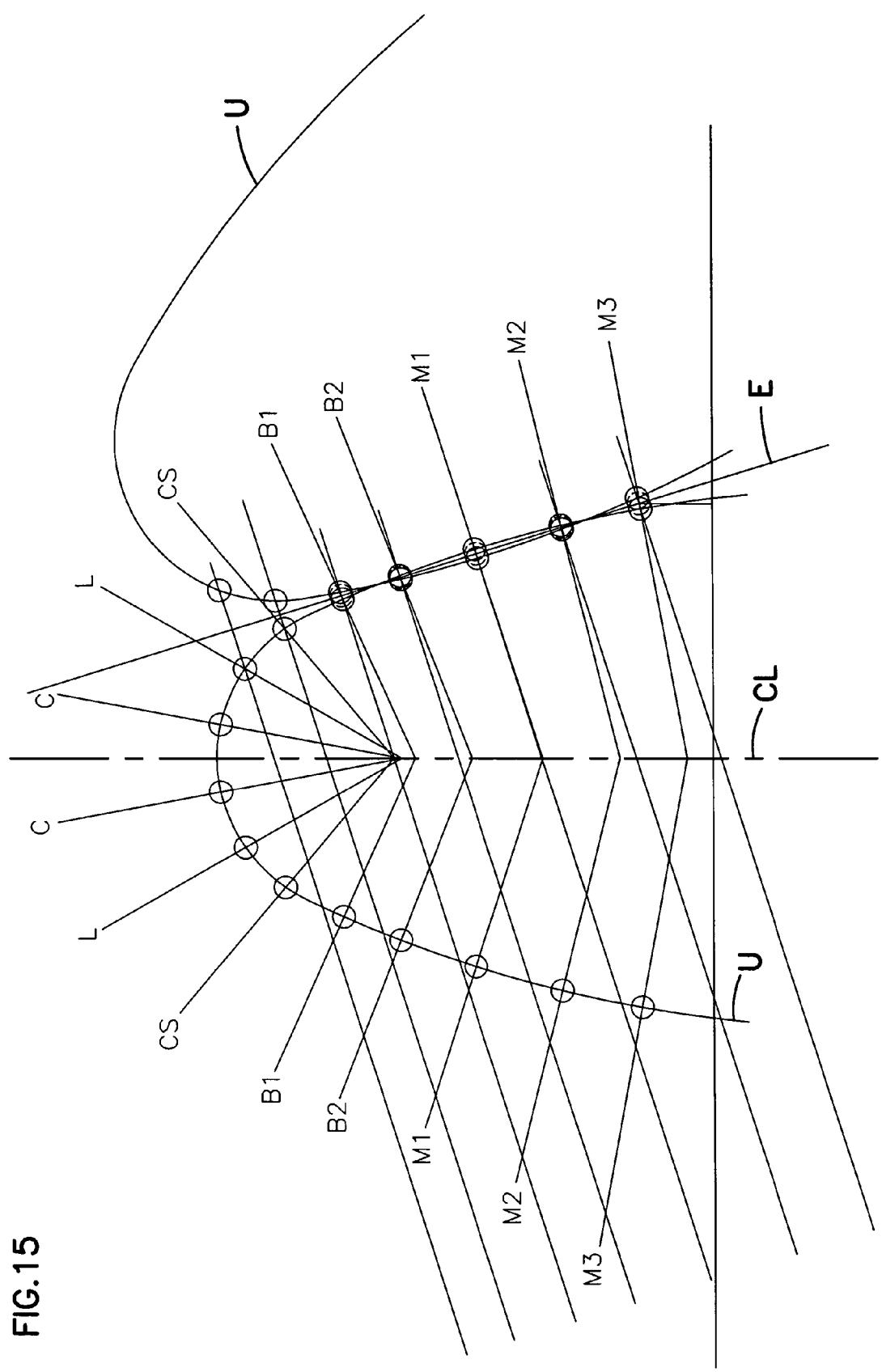
FIG. 15 illustrates the upper hole layout for the upper arc shown in FIG. 14 mirrored to establish a linear array of holes.
Figure 16:
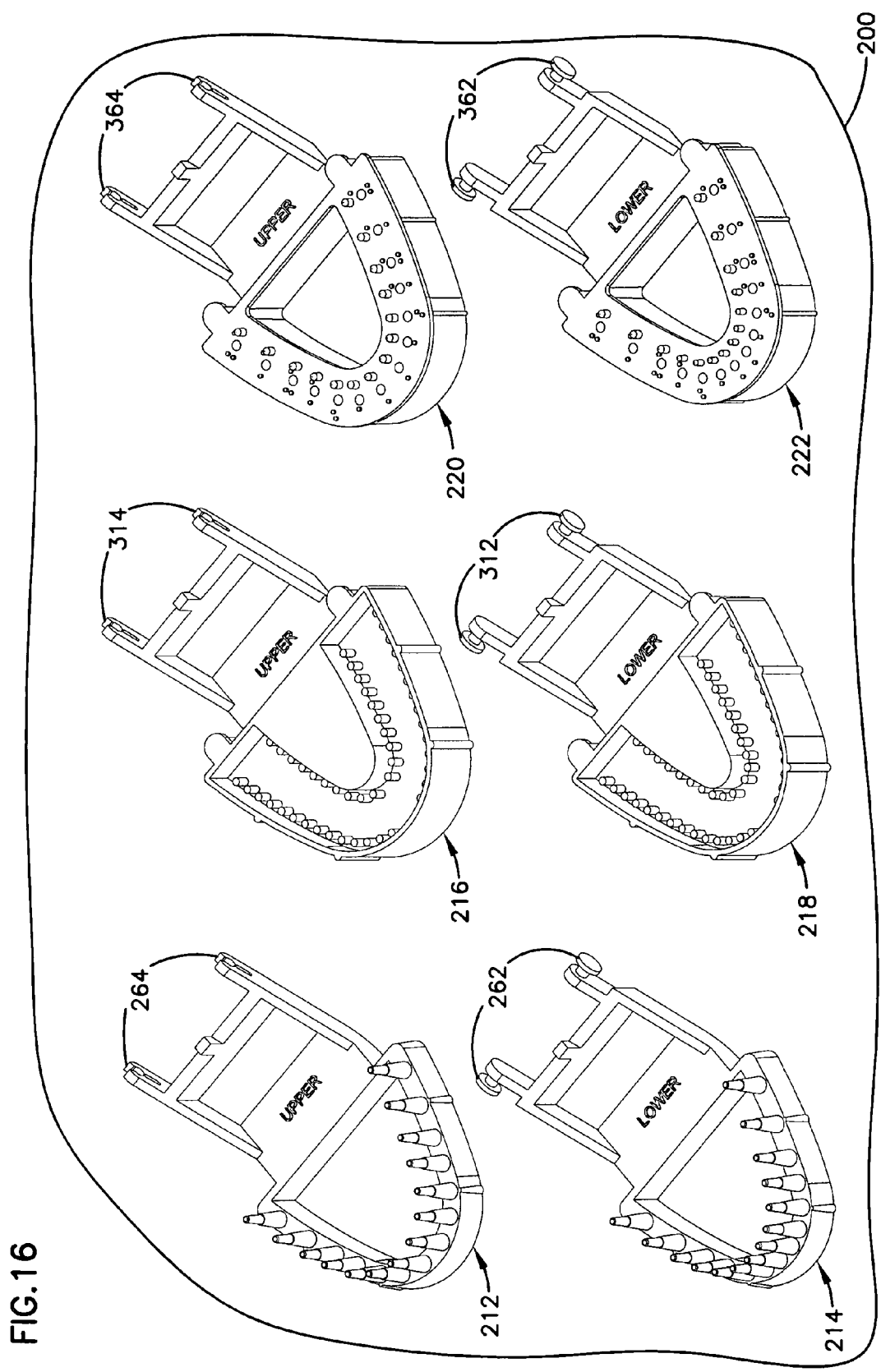
FIG. 16 is a perspective view of another example dental articulator system comprising full arc versions of a pin locator, dental model base, and opposing base for upper and lower dental models.

Referring now to FIGS. 14 and 15, FIG. 14 illustrates hole layouts representing teeth of a medium sized upper and lower tooth arch. The arc corresponding to upper teeth is the arc with the greater radius and the arc for the lower teeth has the lesser radius. Each of the circles along each of the arcs represents an average position of molars M1-M3, bicuspid teeth B1-B2, cuspid teeth CS, lateral teeth L, and central teeth C. Generating the hole placement for large and small sized mouths can be done merely by moving the circles axially along the lines away from or toward the center line CL (see FIG. 14) a prescribed distance.

The linear array of holes 73 of the bases 16, 18 is generated by mirroring the upper or lower arch shown in FIG. 14 about an estimated line E passing through the holes M1-M3 and B1-B2. The circles shown in dashed lines are the average position between the circles on mirrored arches U. The lateral and cuspid circles maintain the same position on the pin locator 12, 14 and dental model bases 16, 18 relative to the line E, while the linear spaced holes (e.g., holes 73) are represented by the dashed line holes in FIG. 15. As mentioned above, the central holes C could also be added to the pin locators 12, 14 in bases 16, 18 using the layout of FIG. 15.

The above example has been described using an opposing base with the pin locator and dental model base to generate the models 6, 8. While the opposing base structure is well suited for supporting an opposing model, alternatively one of the dental model bases 16, 18 can also be used in place of the opposing base. Further, if the mold 24 includes a tooth of interest on both the upper and lower sides 26, 28, using the dental model bases 16, 18 can be desired to provide the removablility of modeled teeth of interest.

As noted with reference to FIG. 1, all of the upper components 12, 16, 20 include a female hinge connector, while the lower components 14, 18, 22 include a male connector. One advantage of separating the male and female connectors onto the upper and lower components, respectively, is to ensure no combination of two upper or two lower components is used inadvertently. By ensuring that an upper component is coupled to a lower component at any given time, there is a greater assurance that the technician will correctly form the resulting models 6, 8 representative of the person's actual teeth captured in the mold 24. An exception to this concern of inadvertent combinations of upper and lower components relates to the opposing bases, which could be interchangeable for use as an upper or lower component in many cases.

Many other hinged configurations are possible in addition to the hinge configuration of FIGS. 1-13. For example, each of the components of assembly 10 could include both a male and female connector so that each of the components could be reversible and used as an upper or lower component. While there may be certain drawbacks related to potentially mismatching upper and lower components, such a configuration would result in fewer overall components for the modeling system. FIGS. 23-42 described in detail below, illustrate some alternative hinge embodiments for a quadrant dental modeling assembly.

II. ARTICULATOR SYSTEM EMBODIMENT OF FIGS. 16-21

Referring now to FIGS. 16-21, a dental modeling assembly 200 is shown and described. Dental modeling assembly 200 includes upper and lower pin locators 212, 214, upper and lower dental model bases 216, 218, and upper and lower opposing bases 220, 222. Each of the components 212, 214, 216, 218, 220, 222 includes a full arc configuration corresponding to the arc of a person's teeth. The upper components 212, 216, 220 represent upper teeth of a person, while the lower components 214, 218, 22 represent lower teeth of a person's mouth. The upper components each include female hinge connectors while the lower components each include male hinge connectors, as described in further detail below.

The upper and lower pin locators 212, 214 include features similar to the pin locator features described in U.S. Published Patent Application No. 2004/0029071, titled DENTAL MODEL POURING JIG, now U.S. Pat. No. 7,108,507, issued Sep. 19, 2006. Some features of the dental bases 216, 218 are similar to those features of U.S. patent application Ser. No. 29/216,697, titled DENTAL MODEL BASE WITH A PLURALITY OF INDEXING PINS, now U.S. Pat. No. D529,177, issued Sep. 26, 2006. Some features of opposing bases 220, 222 are similar to the opposing base disclosed in U.S. Published Patent Application No. 2006/0281043, titled DENTAL MODELING ASSEMBLY AND METHODS, and U.S. application Ser. No. 29/231,950, titled OPPOSING DENTAL MODEL BASE, now U.S. Pat. No. D529,178, issued Sep. 26, 2006. The patent related documents referenced in this paragraph are incorporated herein by reference in their entirety.

A. Pin Locators

Figure 17:
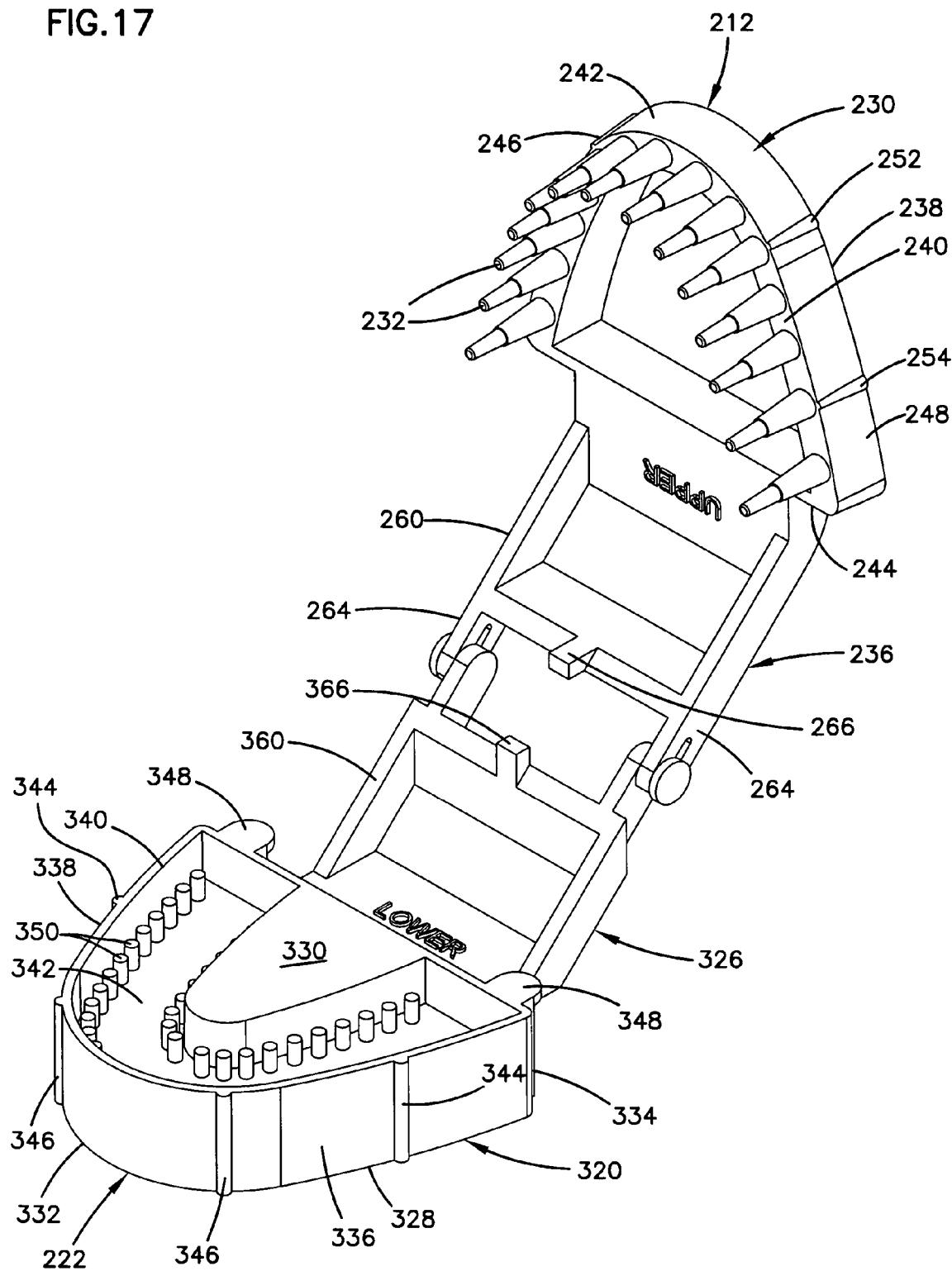
FIG. 17 is a perspective view showing the upper pin locator of FIG. 16 coupled to a lower opposing base with a hinge connection.
Figure 18:
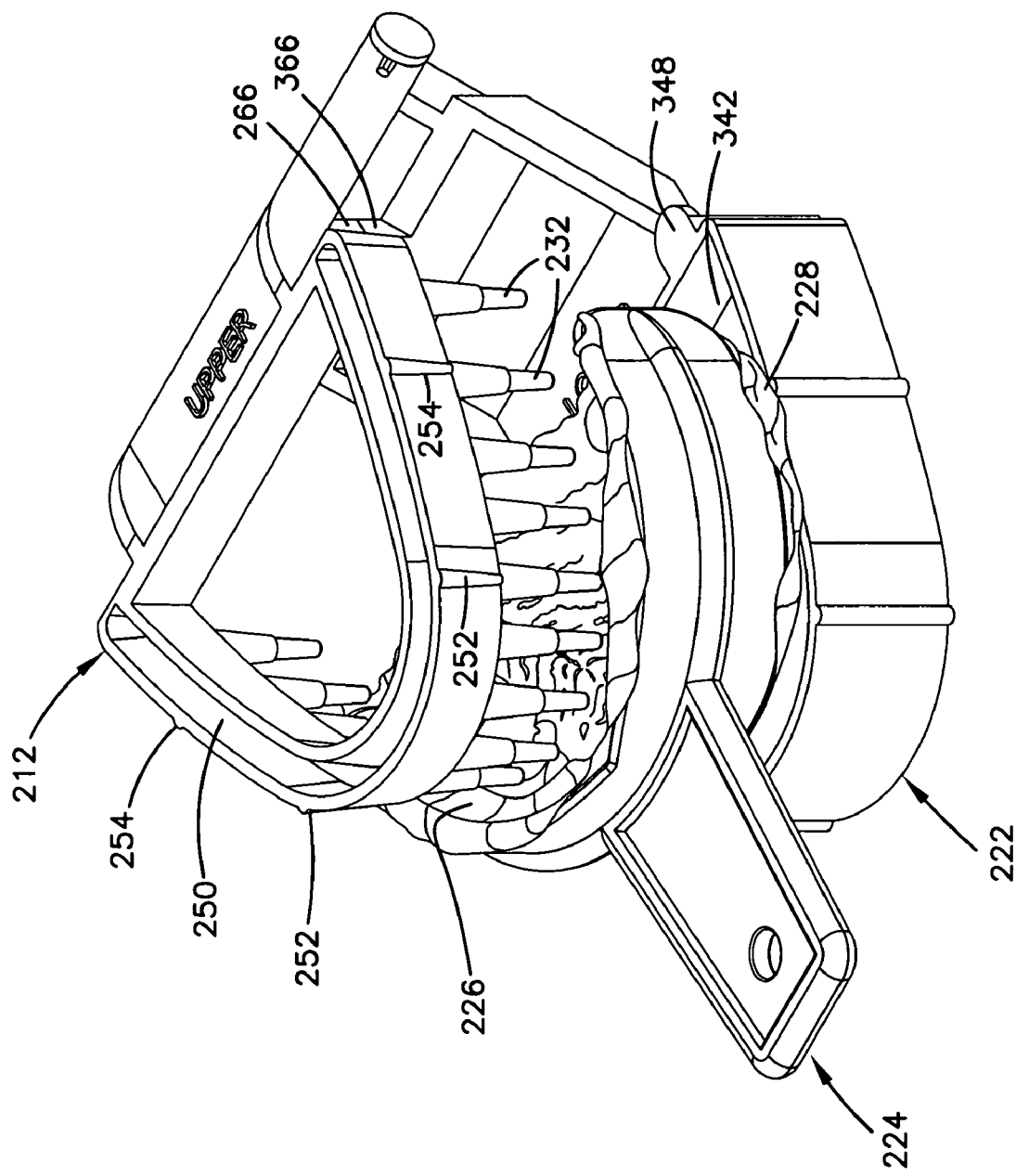
FIG. 18 is a perspective view showing a dental mold oriented between the lower opposing base and upper pin locator.

Referring first to FIGS. 17 and 18, the pin locators 212, 214 include a base member 230, a plurality of locator pins 232, and a hinge portion 236. The base member 230 includes top and bottom sides 238, 240, the bottom side 240 defining a mounting surface, front and rear ends 242, 244, and first and second sides 246, 248. The base member 230 includes cuspid markers 252 and molar markers 254 along each of the sides 246, 248 and in alignment with the locator pins 232 representing the first molar M1 and cuspid tooth CS, respectively, of a person's arc of teeth.

The locator pins 232 can be configured as removable pins that are retained within holes formed in the bottom side 240. In the illustrated embodiment, the locator pins 232 are integrally formed as a single piece with the bottom side 240 of the pin locators 212, 214.

The hinge portions 236 include a connecting arm 260, a male or female hinge connector 262, 264, and a stop member 266. The connecting arm 260 extends from the rear end 244 of the base member 230. The connecting arm 260 can be split into separate arms or legs. While one end of the connecting arm 260 engages the base member 30, an opposing end of the connecting arm 260 includes the stop member 266 mounted thereto and the male or female hinge connector extending therefrom. In some embodiments, the connecting arm 260 can be a solid singular piece without separate leg or arm members. Further, the stop member 266 can be mounted to one of the opposing arm or leg members of the connecting arm 266 rather than on a cross member as shown in the Figures.

B. Dental Model Bases

Figure 19:
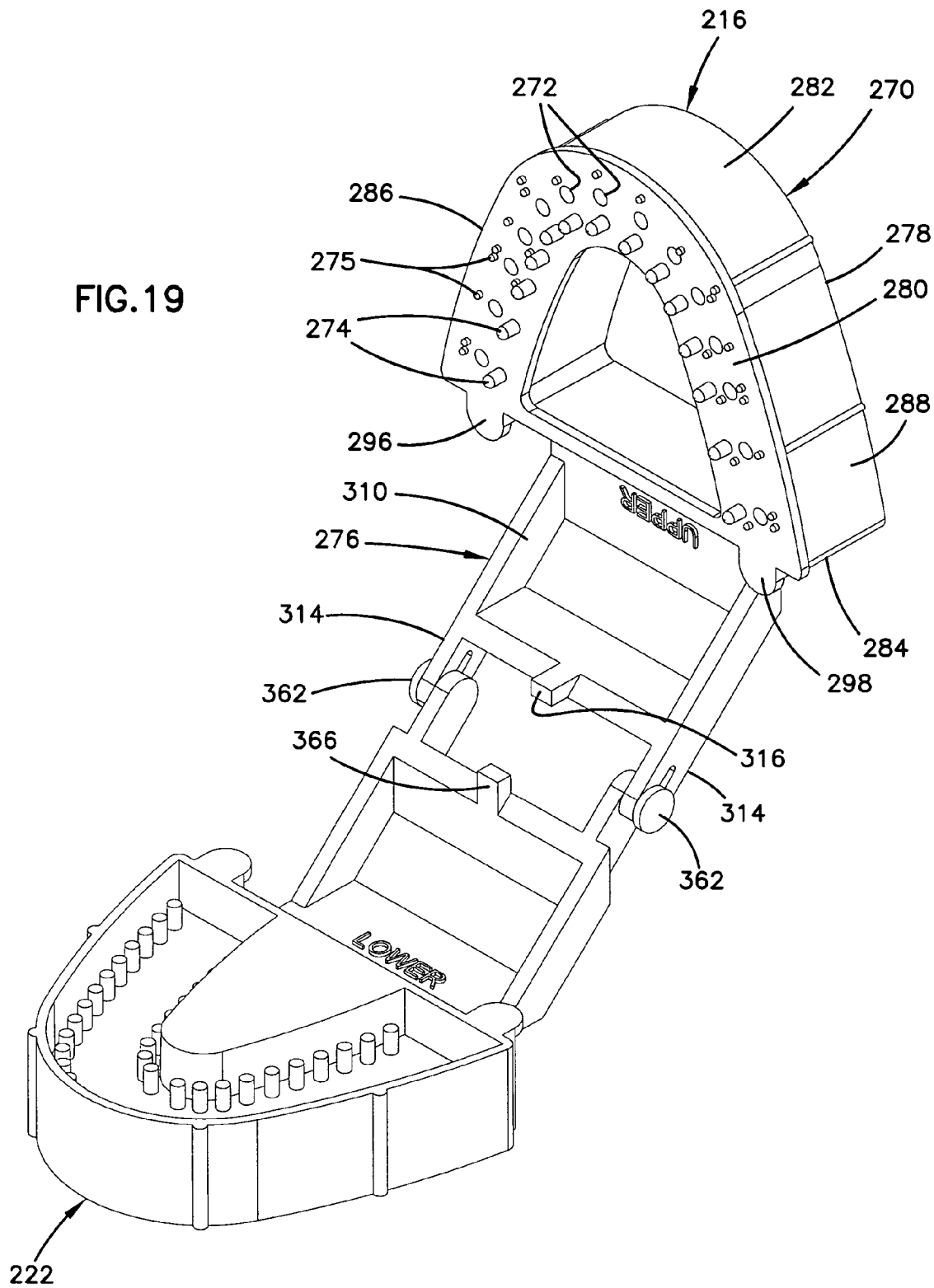
FIG. 19 is a perspective view showing the upper dental model base of FIG. 16 coupled to the lower opposing base with a hinge connection.
Figure 20:
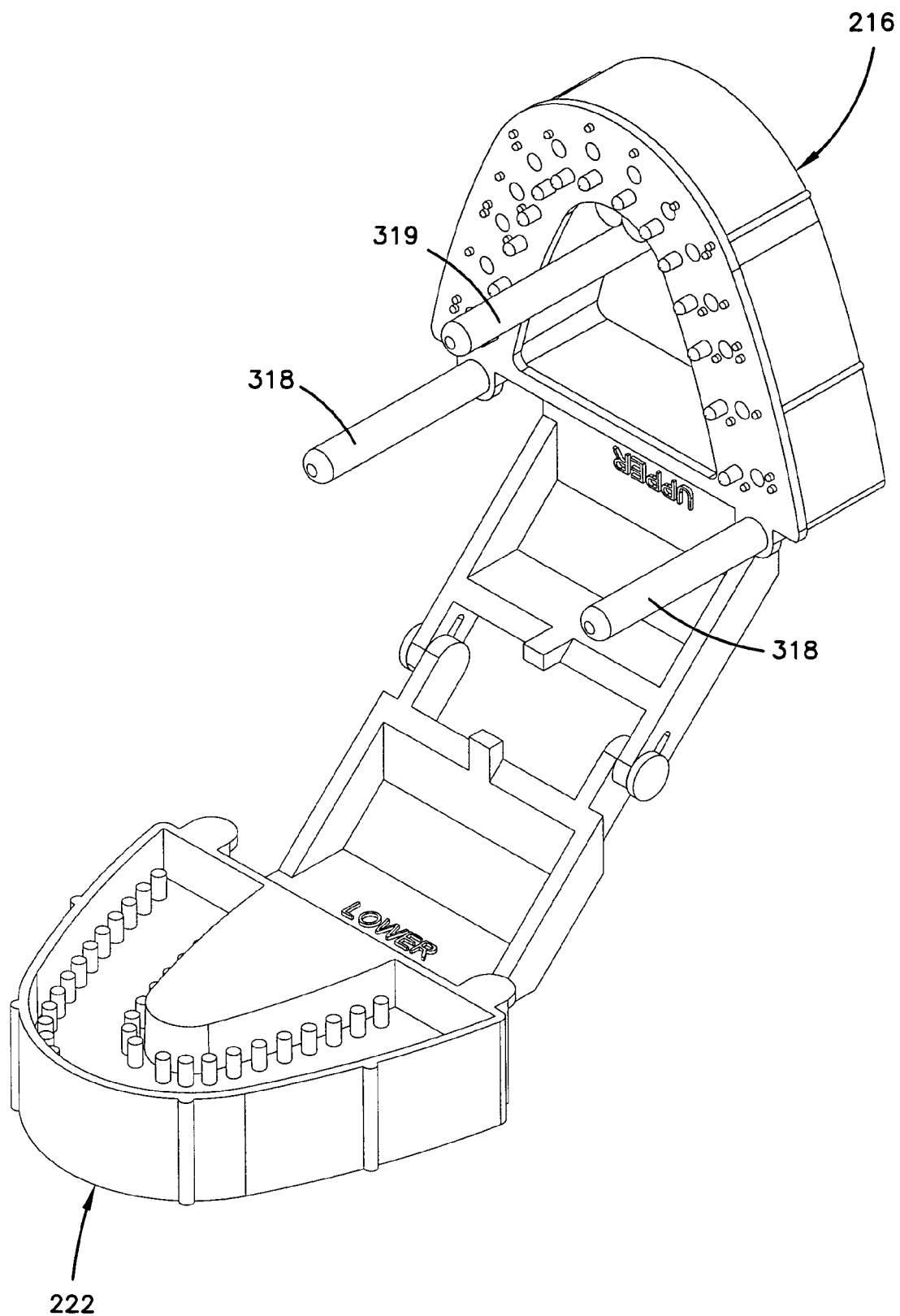
FIG. 20 illustrates the dental model base and opposing base of FIG. 19 with a plurality of stop rods mounted to the dental model base.

The dental model bases 216, 218 are described with reference to FIGS. 19-21. The bases 216, 218 include a base member 270, a plurality of holes 272, a plurality of indexing members 274, 275, and a hinge portion 276.

The base member 270 includes top and bottom sides 278, 280, wherein the bottom side 280 defines a primary mounting surface, front and rear ends 282, 284, and first and second sides 286, 288. The base member 270 also includes a continuous sidewall 290 that extends around an exterior circumference of the base member 70 as well as an interior side thereof to define the cavity 292. A plurality of protrusions 300 protrudes into the cavity 292 beginning at the bottom side 280. Each of the protrusions 300 includes a tapered cavity extending therethrough that is in alignment with one of the plurality of holes 272. The tapered cavities are sized to receive tapered pins, such as tapered pins 115 shown with reference to FIGS. 1-13 above, wherein the tapered pins are retained in the tapered cavities with an interference fit and are removable. At least some of the tapered cavities 300 and associated holes 272 can be replaced with permanently mounted pins. The permanently mounted pins may be especially useful for securing portions of a dental model to the bases 216, 218.

The holes 272 are positioned along the primary mounting surface 280 with a spacing that matches an average position of actual teeth in a person's mouth. Example hole spacings are described with reference to FIGS. 14 and 15. In alternative arrangements, the holes 272 can having different spacings and multiple rows of holes, such as the holes described in U.S. Pat. Nos. 6,471,513 and D452,566, which are incorporated herein by reference. Alternatively, the holes 272 can be drilled into surface 280 after determining an exact position of the hole relative to a tooth of interest in the dental mold as described in U.S. Pat. No. 6,884,068, which is incorporated herein by reference.

The base member 70 further includes spacer rod recesses 296, 298 at opposing front and rear ends 282, 284, and molar markers 294 and cuspid markers 295 on opposing sides 286, 288. The spacer rod recesses 296, 298 are sized to receive spacer rods 318, 319 as shown in FIGS. 20 and 21. The markers 294, 295 are aligned with holes 70 corresponding to the first molar and cuspid member of a person's teeth.

C. Opposing Bases

Figure 21:
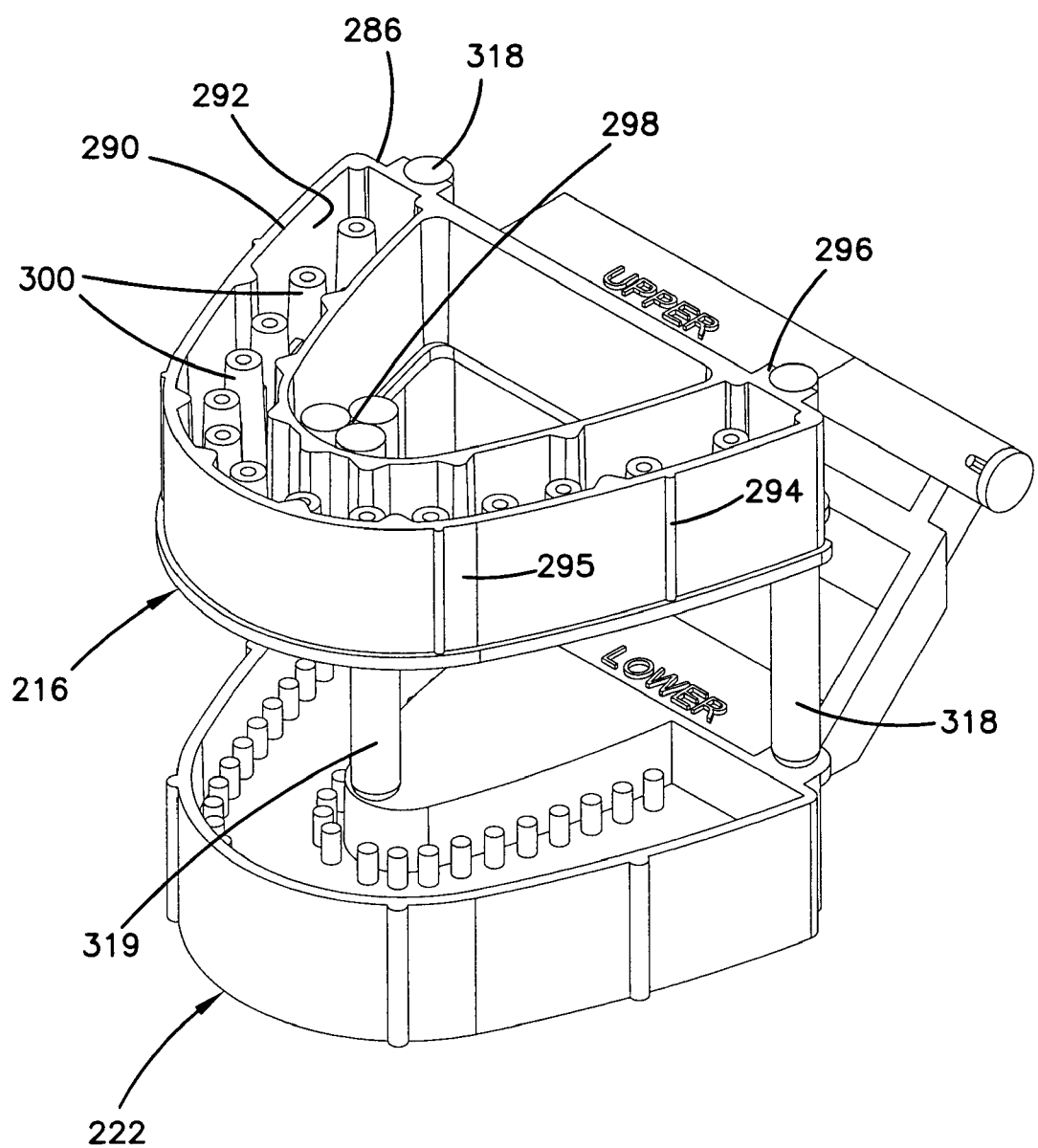
FIG. 21 illustrates the dental model base and opposing base of FIG. 20 in the closed position with ends of the stop rods engaging the opposing base.

Referring now to FIGS. 17-21, the opposing base 220, 222 each include a base member 320 and a hinge portion 326. The base member 320 includes top and bottom sides 328, 330, the bottom side 330 defining a mounting or engagement surface, front and rear surfaces 332, 334, and first and second sides 336, 338. The base member 320 also includes a recessed floor 342 defined by continuous sidewall 340. A plurality of engagement pins 350 extend from the recessed floor 342 in rows adjacent to the continuous sidewall 340. The base member 320 includes spacer rod contacts 348 sized to engage ends of spacer rods 318, 319 as shown in FIG. 21. Molar markers 344 and cuspid markers 346 are included along the first and second sides 336, 338 for helping in aligning with first molar and cuspid teeth impressions of a dental mold such as mold 224 shown in FIG. 18.

The hinge portion 326 includes a connecting arm 360, male or female hinge connectors 362, 364, and stop member 366. The features of hinge portion 326 can be the same or similar to the features of hinge portion 236 of the pin locators and hinge portion 276 of the dental model bases 216, 218 described above. The stop member 366 is configured to engage the stop member 266 of the pin locators 212, 214 or the stop member 316 of the dental model bases 216, 218, depending on which of the components is coupled to the opposing base at any given time.

D. Dental Mold

The use of dental modeling assembly 200 for generating models of upper and lower teeth from a full arc dental mold 224 has many similarities to methods described above with reference to dental modeling assembly 10. The dental modeling assembly 200 is particularly well suited for modeling the anterior teeth (i.e., the central, lateral and cuspid teeth), while still being capable of modeling the posterior teeth (i.e., the bicuspid and molar teeth).

E. Dental Modeling Methods

An initial step in the process of modeling using the dental modeling assembly 200 is to select the proper pin locator 212, 214. The pin locators 212, 214 are held in alignment with teeth impressions of a mold 224 to make this determination. In addition to different upper and lower pin locators 212, 214, other considerations can include the size of the pin locators 212, 214. As described above with reference to FIGS. 14 and 15, it is possible to make different sized upper and lower pin locators, dental model bases, and opposing bases that correspond to, for example, small, medium and large size mouths. Thus, one way of optimizing the dental modeling method is to select not only between the upper and lower pin locators, but also select among the different sizes of pin locators that are available.

After the proper pin locator 212, 214 is selected (the upper pin locator 214 being used with reference to FIGS. 17 and 18), the pin locator is coupled to an opposing base 220, 222 (the lower opposing base 222 being illustrated in FIGS. 17-21), with the female hinge connector 264 of the pin locator in hinged or pivotal connection with the male hinge connector 362 of the opposing base 222. The dental mold 224 is held in position between the locator pins 232 of the pin locator and the opposing base 222 with the locator pins 232 aligned with the teeth impressions of the mold 224. If any trimming of the mold 224 is required to eliminate interference between the mold and the pin locator and opposing base, those modifications are made before the lower side impression 228 and opposing base 222 are filled with a first moldable material. The filled lower side 228 is then brought into engagement with the filled opposing base 222. The mold 224 is adjusted relative to the locator pins 232 for proper alignment with the teeth impressions of the mold, and the first moldable material is allowed to set to form a lower dental model (not shown).

The pin locator 212 is then replaced with the upper dental model base 216 so that a hinged or pivotal connection between the upper dental model base 216 and the lower opposing base 222 exists. Removable pins are added to the plurality of holes 272 of the dental model base that correspond to at least the impression of the damaged tooth of interest in the mold upper side impression 226. Removable pins can be added to any one of the plurality of holes 272 to provide removability of the resulting teeth models formed from the upper side impression 226 of the mold 224. The dental model base 216 is then rotated into a closed position with the primary surface 280 in a parallel arrangement relative to the bottom surface 330 of the opposing base. A visual check is conducted to ensure that there is no obstruction between the mold 224 and the dental model base 216 or the removable pins secured in holes 272 of the dental model base. Typically, the stops 316 and 366 of the dental model base 216 and opposing base 222, respectively, provide sufficient parallel alignment between the bases 216, 222. However, it may be necessary to use additional stop members such as stop rods 318, 319 (see FIGS. 20 and 21) to more accurately define the parallel orientation.

Next, the upper side impression 226 of the mold 224 is filled with a second moldable material (not shown) and the primary surface 280 of the dental model base along with the exposed ends of the tapered pins inserted in the plurality of holes 72 and corresponding indexing members 274, 275 adjacent to those exposed tapered pins are also covered with the second moldable material. The moldable dental model base 216 is again rotated into the closed position to engage the second moldable material on the base 216 with the moldable material in the upper side impression 226 of the mold 224. The technician conducting these modeling steps can check the parallel arrangement between the surfaces 280 and 330 of the bases 216, 222, respectively, by engagement of the stop members 316, 366 and engagement of ends of the stop rods 318, 319 with contact surfaces 348 of the opposing base 222.

The second moldable material is cured to generate an upper dental model, and the mold 224 is removed from the upper and lower models. The upper and lower models (not shown) can then be articulated relative to each other while the bases 216, 222 are coupled together with the hinge connection.

As with the dental modeling assembly 10 described above, the assembly 200 can function adequately when the opposing bases 220, 222 are replaced by one of the dental model bases 216, 218. For example, in the examples shown in FIGS. 18-21, the lower opposing base 222 could be replaced with a lower dental model base 218. Such a replacement may be desired if preparing a damaged tooth of interest from the lower side impression 228 as well as the upper side impression 226.

The hinge features of hinge portions 236, 276 and 126 can be altered in other embodiments. For example, each of the upper and lower components of the assembly 200 could include one female hinge connector and one male hinge connector to improve interchangeability of some of the components, such as the opposing base, thereby requiring only a single opposing base rather than two separate components as is required by the example system 200 shown in FIG. 16.

The hinge portions 236, 276, 326 have a maximum width that is no greater than a maximum width of each of the base members 230, 270, 320. As a result, the hinge portions minimize obstruction of a grinding wheel when grinding excess portions of the first or second moldable material from the completed upper and lower dental models.

The male and female hinge connectors used in the dental modeling assemblies 10, 200 provide for a snap-fit connection. The interface between the male and female hinge connectors possess relatively tight tolerances that result in negligible, imperceptible lateral movement of the upper and lower components relative to each other.

The components of modeling assemblies 10, 200 can comprise a polymer base material such as, for example, nylon, polycarbonate plastics, or other castable or injection moldable materials. Preferably, the pin locator is made of a material that provides properties of high strength and rigidity, and transparency.

While features of the pin locators, dental model bases and opposing bases are formed as a single unitary piece. Thus, there is no requirement for connecting the features of each of the components together such as, for example, securing the hinge portion 36 of the pin locators 12, 14 to the base member 30, because those features are integrally formed as a single piece. The only coupling or otherwise connection required in the assemblies 10, 200 is the hinge connection of male and female hinge connectors between the upper and lower components. While this single unitary piece construction is preferred, it is possible in alternative embodiments to make various features of each of the components as separate pieces and then secure those pieces together in subsequent steps during the process of manufacturing the components. For example, the connecting arms 60 of the hinged portion 36 of the pin locators 12, 14 could be secured to a rear end 44 of the base member 30 using, for example, an adhesive or a snap-fit connection so that the otherwise two separate pieces are coupled together to form a single one of the pin locators 12, 14. By generating the components in separate pieces in this manner, it may be possible to provide different types of hinge portion designs for different types of modeling methods or systems using the same base and pin portion. For example, one hinge portion design can have a connector arm angle β (see FIG. 4A) that is relatively large when dealing with triple tray molds versus a relatively small angle β when handling a mold with an impression of only one of the upper or lower sides of a person's teeth.

III. ALTERNATIVE HINGE EMBODIMENTS

FIGS. 22-42 illustrate several alternative hinge designs for use with the dental modeling systems disclosed above. While the particular configurations of FIGS. 22-42 are sized specifically for quadrant versus full arc style components, these hinged designs can be modified for use with a full arc component such as the components 212, 214, 216, 218, 220, 222 described with reference to FIGS. 16-21.

Each of the embodiments shown in FIGS. 22-42 is a hinge assembly 400 that generally includes first and second connecting arms 402, 404, first and second male hinge members 410, 412, first and second female hinge members 414, 416, and first and second stop members 418, 420. Each of the connecting arms 402, 404 includes a base attachment portion 406 and hinge attachment portion 408. Some of the embodiments can include first and second stop surfaces 422, 424 and lateral stabilizing members 426, 428.

A. Embodiment of FIGS. 22-24

Figure 24:
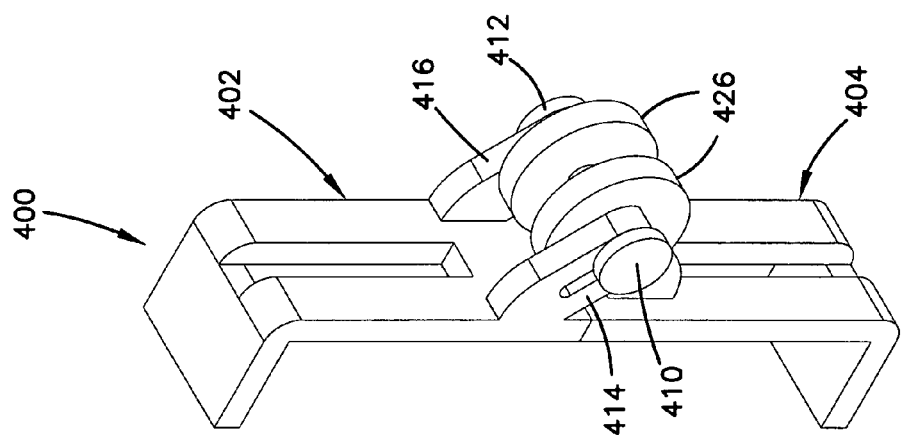
FIGS. 22-24 illustrate another example hinge assembly embodiment according to inventive principles disclosed herein.
Figure 23:
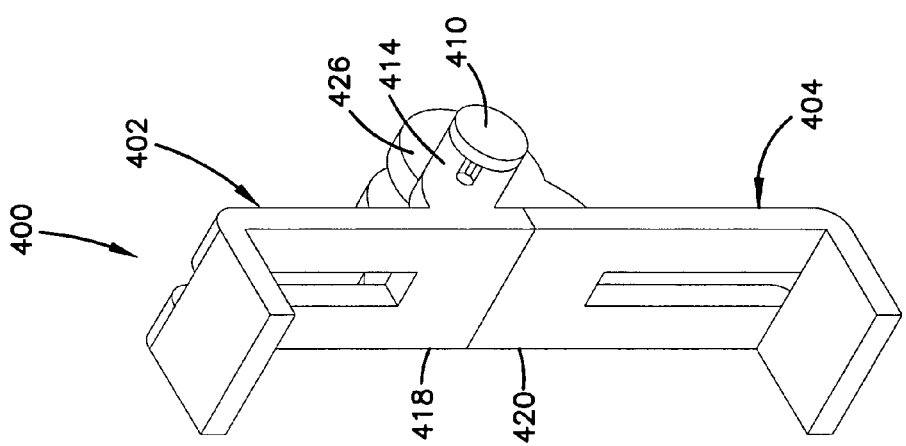
Figure 22:
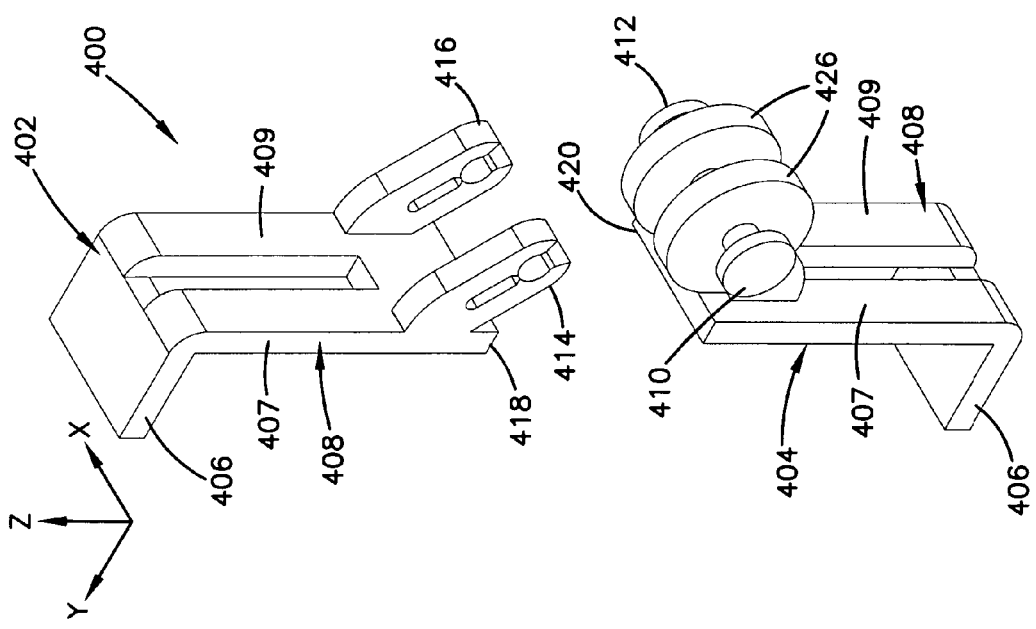

Referring first to FIGS. 22-24, the hinge assembly 400 includes hinge attachment portions 408 that extend in a generally perpendicular direction relative to the base attachment portion 406. An end of the hinge attachment portion 408 defines the stop members 418, 420. The hinge members 410, 412, 414, 416 extend at an angle relative to the hinge attachment portion 408, which is alternatively described as extending in a non-parallel direction relative to the hinge attachment portion 408.

The first connecting arm 402 includes both female hinge members 414, 416 while the second connecting arm 404 includes both of the male hinge members 410, 412. The configuration of the hinge assembly 400 of FIGS. 22-24 is similar to the hinge features of assembly 10 described above. Lateral stabilizing members 426 define part of the male hinge members 410, 412. The stabilizing members 426 help control movement of the female hinge members 414, 416 in the lateral direction. The female hinge members 414, 416 are configured to snap-fit onto the male hinge members 410, 412.

The hinge attachment portions 408 each include a slot formed therein defining legs 407, 409. The legs 407, 409 have a width dimension in the X direction that is greater than a thickness dimension in the Y direction (when viewing the closed orientation of FIGS. 22-24). As a result, the hinge assembly 400 of FIGS. 22-24 can provide greater flexibility in the Y direction than in the X direction. Such inherent flexibility can provide certain advantages or disadvantages for a dental modeling assembly component (e.g., a pin locator or dental model base) to which the hinge assembly 400 of FIGS. 22-24 is connected. Some such advantages or disadvantages include the ability to articulate the models mounted to the dental modeling assembly components.

B. Embodiment of FIGS. 25-27

Figure 27:
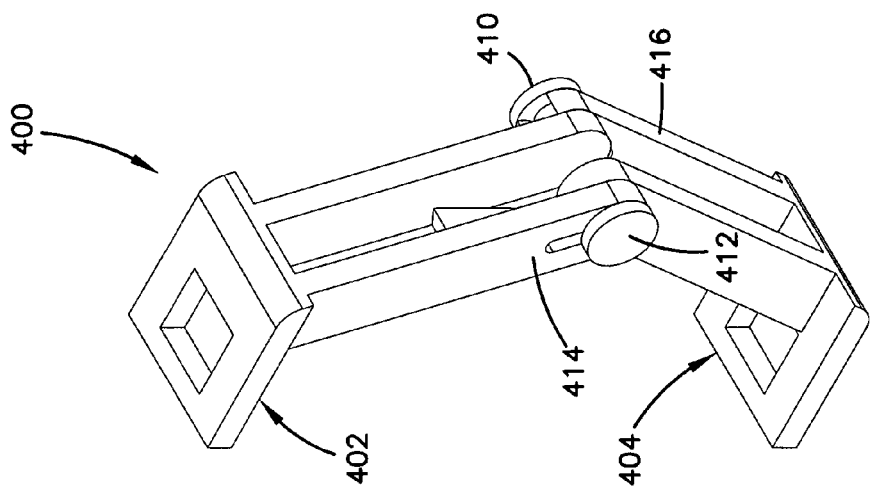
FIGS. 25-27 illustrate another example hinge assembly embodiment according to inventive principles disclosed herein.
Figure 26:
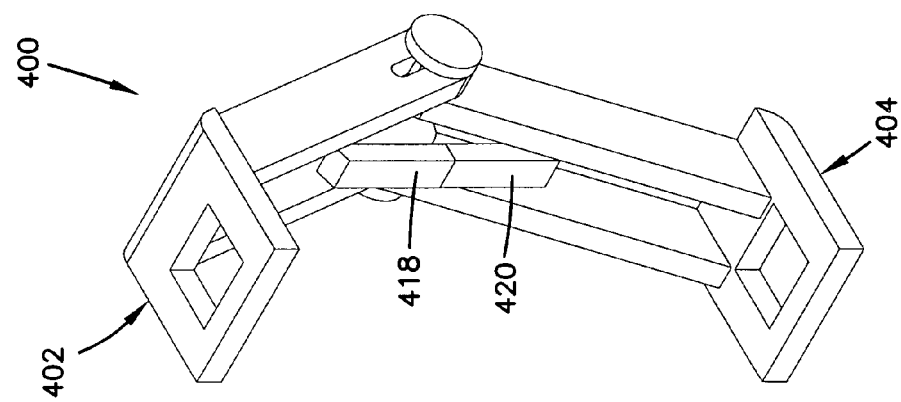
Figure 25:
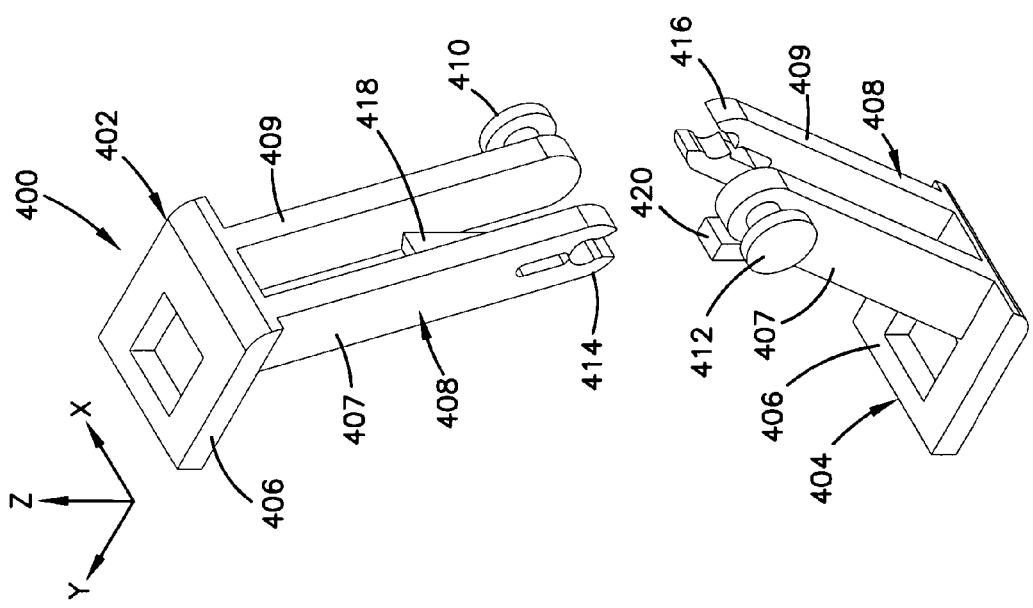

Referring now to FIGS. 25-27 another hinge assembly embodiment 400 is shown and described. Assembly 400 of FIGS. 25-27 includes a hinge attachment portion 408 that is divided into separate arms 407, 409. The arms 407, 409 each have a width dimension in the X direction that is less than a thickness dimension in the Y direction. This construction can provide for increased flexibility in the X direction versus in the Y direction.

A separate stop member 418, 420 is positioned between the arms 407, 409. The stop members extend in a direction substantially parallel to the Z axis when the connecting arms 402, 404 in the closed position shown in FIGS. 22-24.

The arms 407, 409 extend at an angle direction relative to the Z axis and in the Y direction. Angled hinge attachment portions 408 can provide for reduced chances of obstructing the dental mold or the resulting dental models used and formed during a dental modeling process using, for example, one of the modeling assemblies 10, 200 described above.

Each of the arms 407, 409 of the hinge attachment portion 408 have a separate male and female hinge member at an end thereof. The first and second connecting arms 402, 404 are mirror images of each other and could be interchangeable.

The female hinge members 414, 416 are configured to snap-fit onto and off of the male hinge members.

C. Embodiment of FIGS. 28-30

Figure 30:
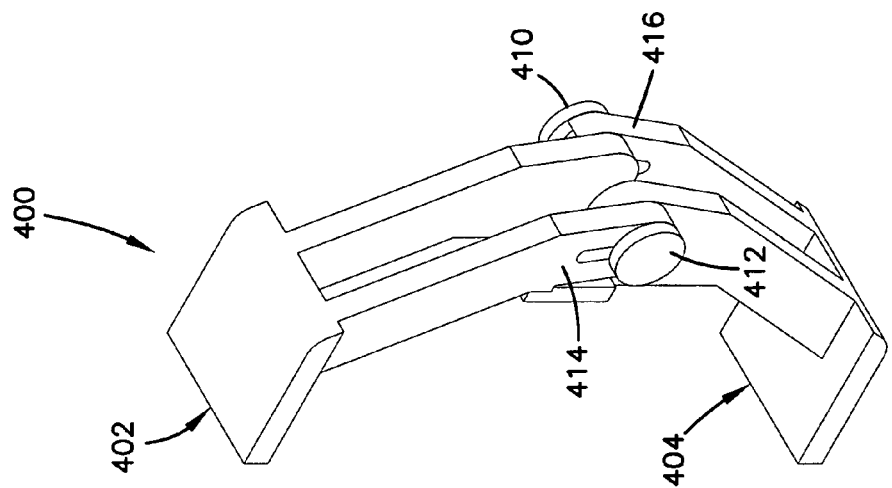
FIGS. 28-30 illustrate a still further hinge assembly embodiment according to inventive principles disclosed herein.
Figure 29:
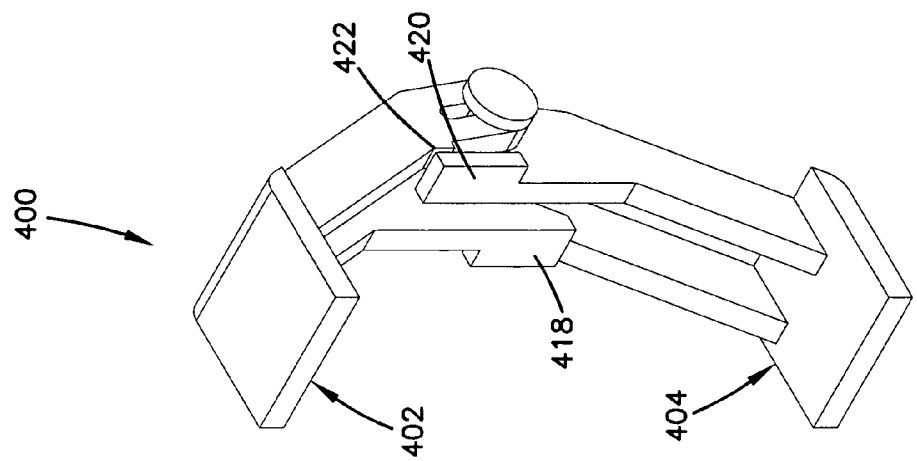
Figure 28:
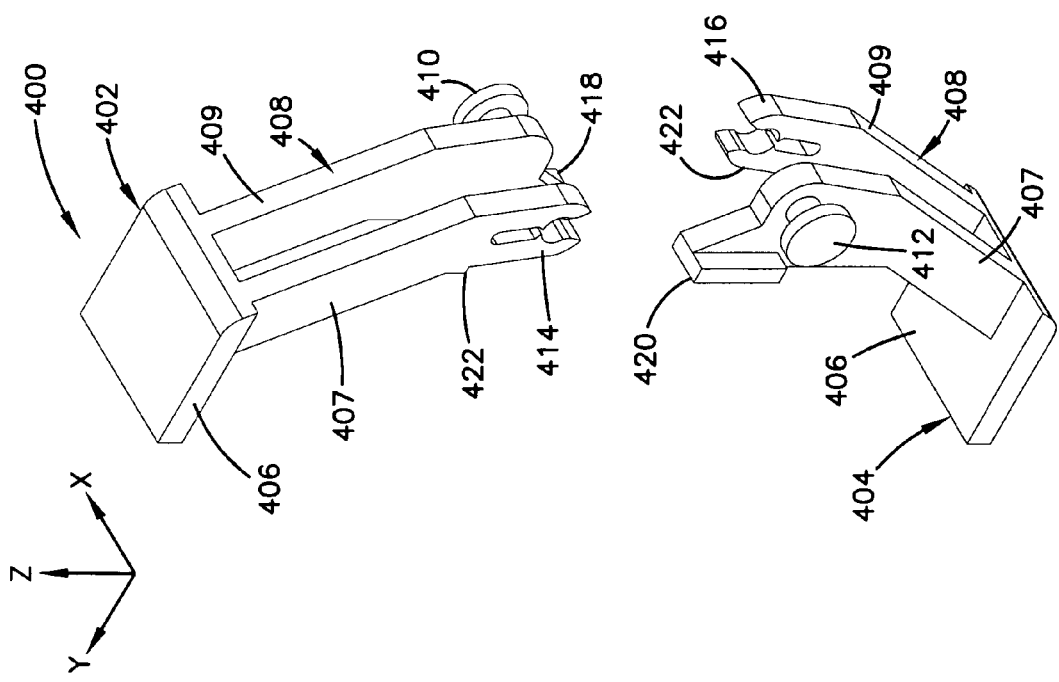

Referring now to FIGS. 28-30, another example of hinge assembly 400 is shown and described. The arms 409 of the hinge attachment portions 408 each include one of the stop members 418, 420 and the arm 407 includes a stop surface. The engagement of stop members 418, 420 with the stop surfaces 422, 424 in the Y direction limits relative rotation of the connecting arms 402, 404. Engagement in the Y direction is different from engagement of stop members 418, 420 in the Z direction as illustrated in the embodiments of FIGS. 22-27. The stop members 418, 420 of FIGS. 28-30 could be used in combination with separate stop members or stop features providing engagement in the Z direction.

Each of the connecting hinge attachment portions 408 includes a portion of the length that extends in a direction non-perpendicular to the base attachment portion 406, and a separate portion along its length that extends in a perpendicular direction relative to base attachment 406. The portion that extends perpendicular mounts the male and female hinge members 410, 412, 414, 416. The male and female hinge members are configured for a snap-fit connection relative to each other.

D. Embodiment of FIGS. 31-33

Figure 33:
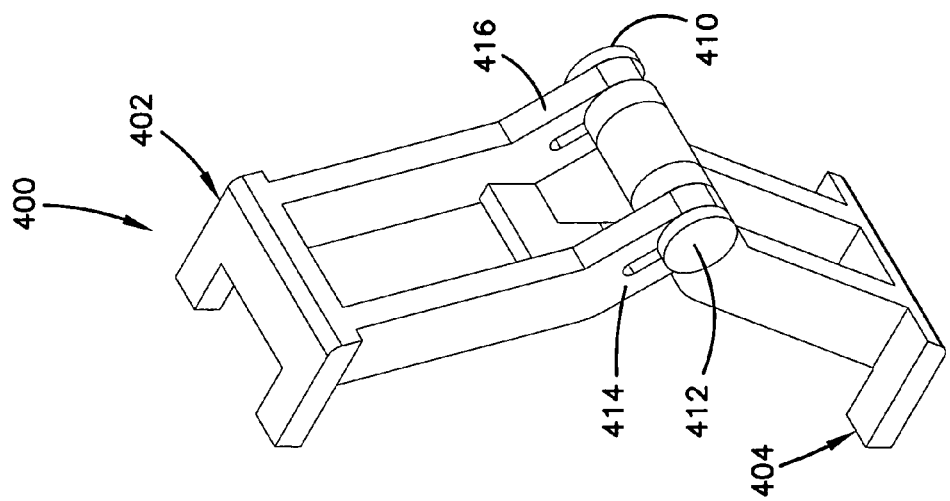
FIGS. 31-33 illustrate another example hinge assembly embodiment according to inventive principles disclosed herein.
Figure 32:
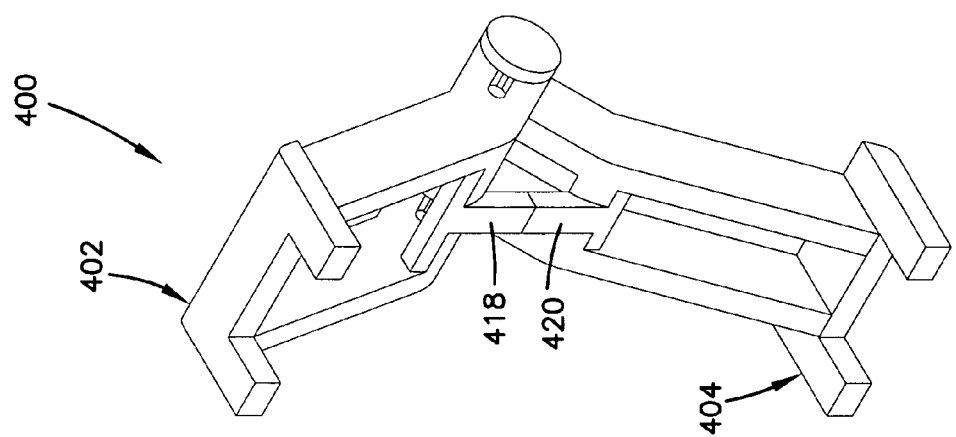
Figure 31:
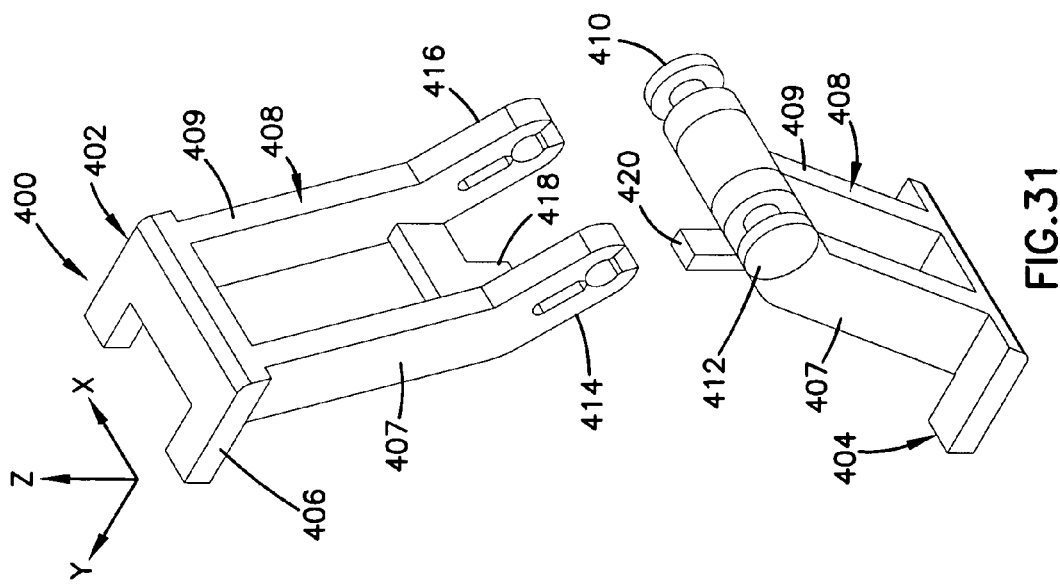

Referring now to FIGS. 31-33, another example of hinge assembly 400 is shown and described. The hinge assembly 400 of FIGS. 31-33 includes hinge attachment portions 408 divided into separate arms 407, 409. Each of the arms 407, 409 includes a first portion along its length that extends at a first non-perpendicular angle relative to the base attachment portion 406, and a second portion along its length that extends at a different non-perpendicular direction relative to the attachment portion 406. In one example, the first portion along the length of the arms 407, 409 extends at an angle of about 95 to 110 degrees and a second portion extends at an angle of about 125 to 145 degrees. Both the female hinge members 414, 416 are included on the first connector arm 402 and both male hinge members 410, 412 are included on the second connecting arm 404. The stop members 418, 420 are arranged in a direction generally perpendicular with the base attachment portion 406 so as to extend in the Z axis when the hinge assembly 400 is in the enclosed orientation shown in FIGS. 31-33.

E. Embodiment of FIGS. 34-36

Figure 36:
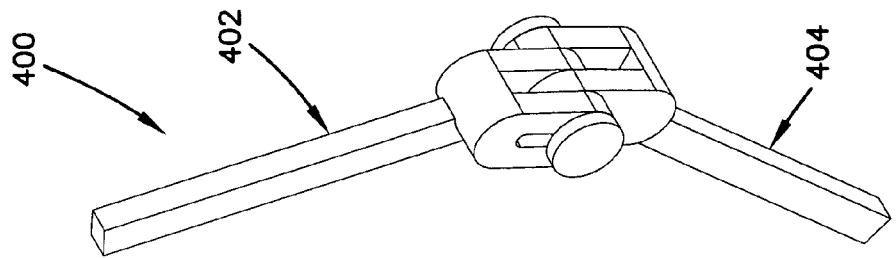
FIGS. 34-36 illustrate a yet further hinge assembly embodiment according to inventive principles disclosed herein.
Figure 35:
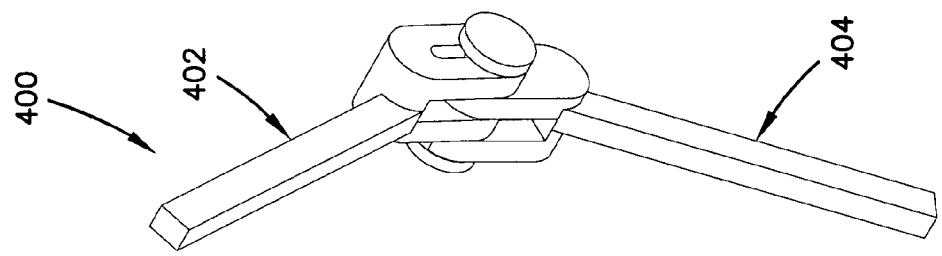
Figure 34:
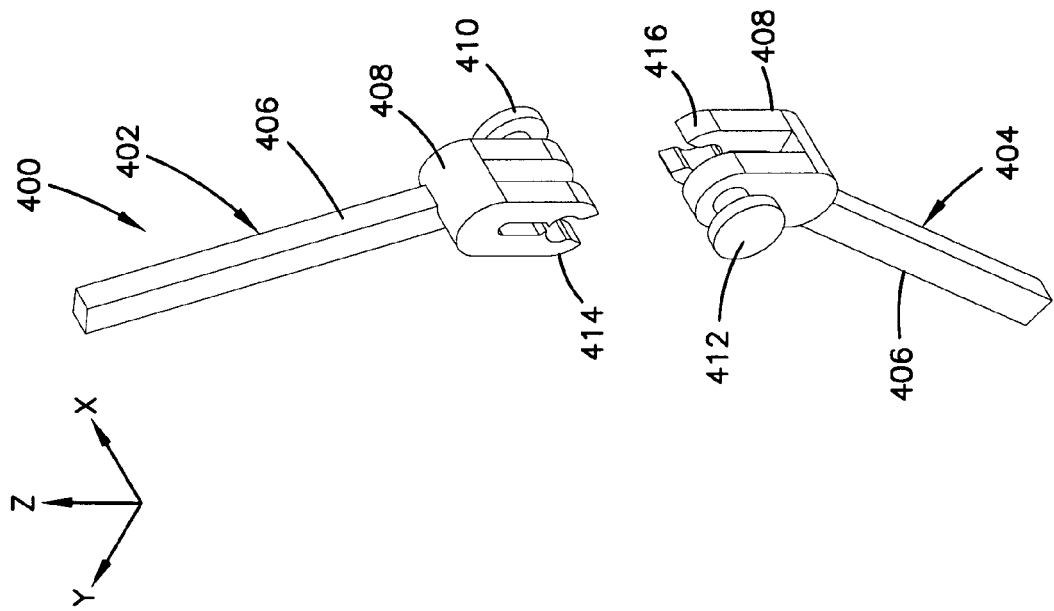

Referring now to FIGS. 34-36. A further hinge assembly embodiment 400 is shown and described. The first and second connecting arms 402, 404 include a base attachment portion 406 that is configured as an elongate rod, and a hinge attachment portion 408 that has the hinge members 410, 412, 414, 416 integrated therein. Each of the connecting arms 402, 404 includes a male hinge member and a female hinge member.

While the hinge assembly 400 of FIGS. 34-36 does not illustrate stop members that restrict relative rotational movement of the connecting arms 402, 404, such stop members could be included in other embodiments. For example, stop members could extend in the Z direction from each of the base attachment portions 406 when the hinge assembly 400 is in the orientation shown in FIGS. 34-36. The stop members engage each other to inhibit relative rotation.

F. Embodiment of FIGS. 37-39

Figure 39:
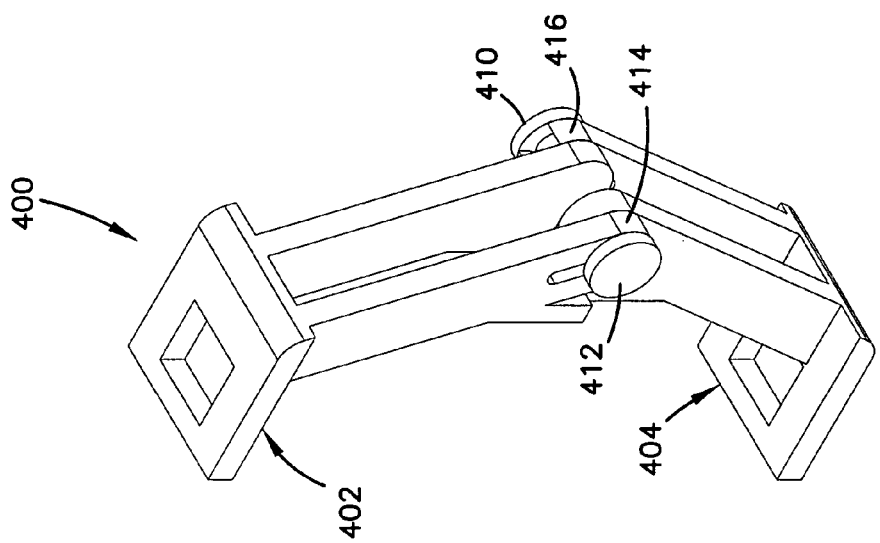
FIGS. 37-39 illustrate another hinge assembly embodiment according to inventive principles disclosed herein.
Figure 38:
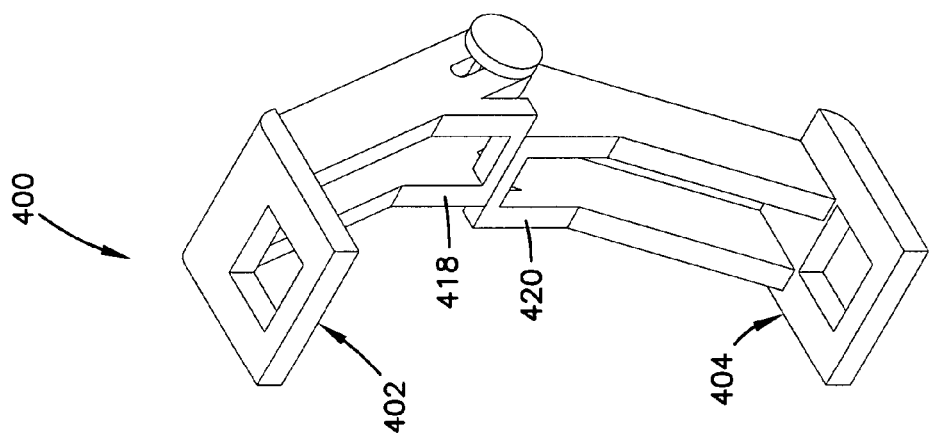
Figure 37:
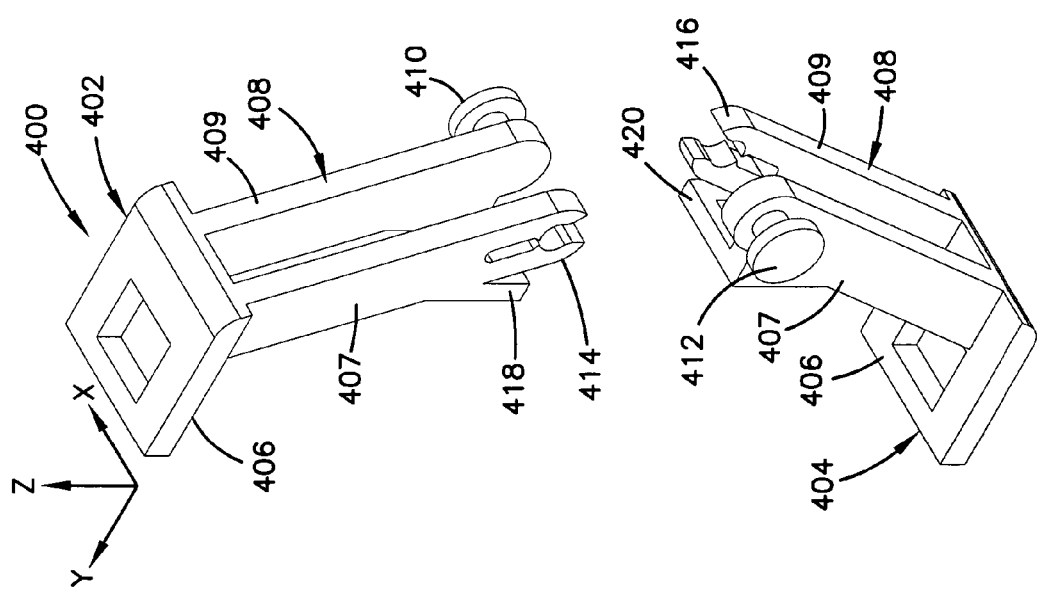

Referring now to FIGS. 37-39, a still further hinge assembly embodiment 400 is shown and described. The hinge assembly 400 of FIGS. 37-39 includes a hinge attachment portion 408 divided into separate arms 407, 409. The arms 407, 409 have a greater thickness dimension in the Y direction than the width dimension in the X direction. Further, the arms 407, 409 include one of the male and female hinge members. The arms 407, 409 are coupled together with the stop members 418, 420. The stop members extend in the Z direction when the hinge assembly 400 is in the orientation shown in FIGS. 37-39. The stop members 418, 420 restrict relative rotation of the first and second connecting arms 402, 404 in at least one direction that provides a parallel orientation of the base attachment portion 406 of each of the connecting arms 402, 404.

The hinge attachment portion 408 extends at an angle different from a perpendicular orientation relative to the base attachment portion 406.

The arms 407, 409 are arranged in offset planes relative to the arms 407, 409 of the opposed connecting arms 402, 404. Likewise, the stop members 418, 420 are offset in the X direction relative to each other.

G. Embodiment of FIGS. 40-42

Figure 42:
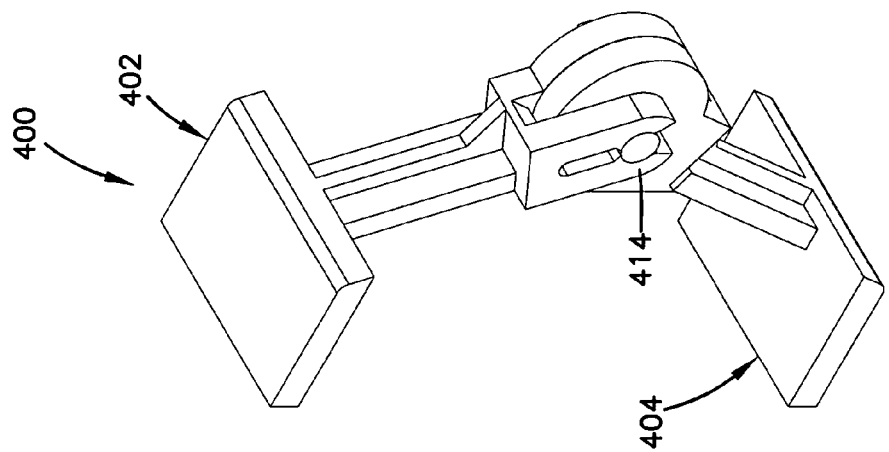
FIGS. 40-42 illustrate another example hinge assembly embodiment according to inventive principles disclosed herein.
Figure 41:
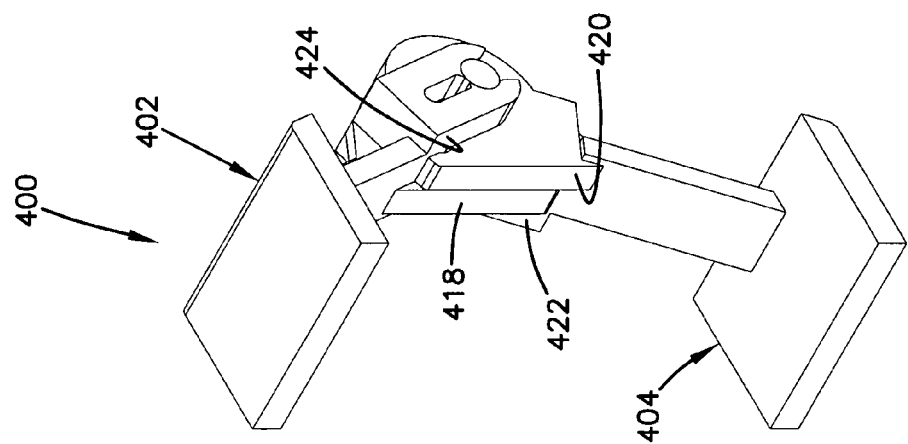
Figure 40:
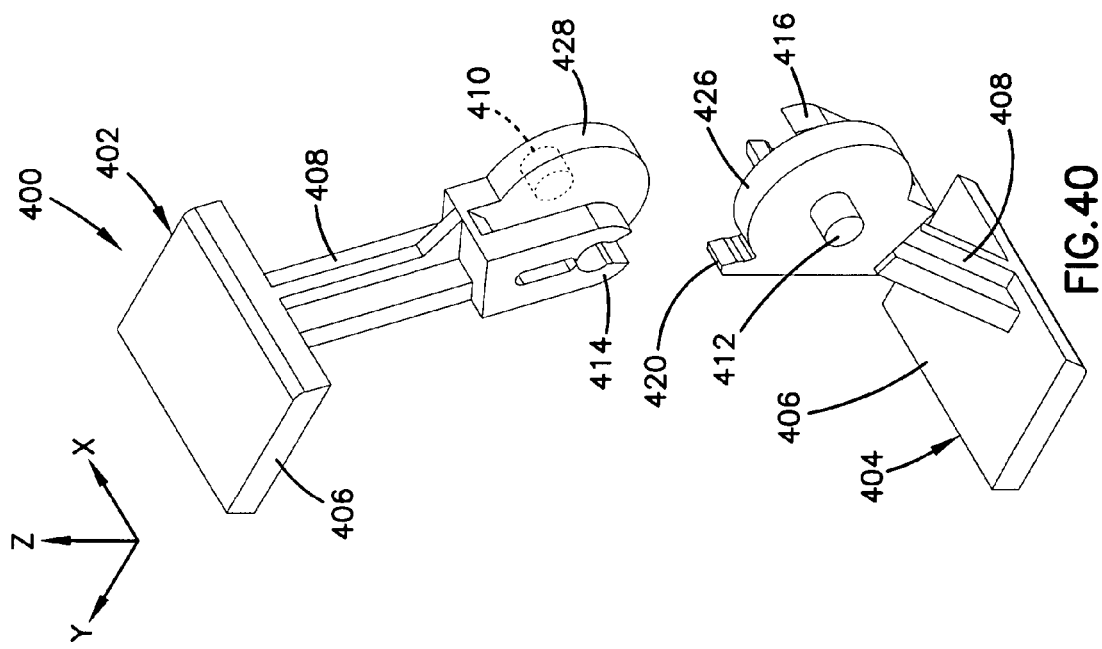

Referring now to FIGS. 40-42, a further hinge assembly embodiment 400 is shown and described. The assembly 400 of FIGS. 40-42 includes a hinge attachment portion 408 that is a unitary piece not divided into separate arms. The hinge attachment portion 408 extends at an angle that is not perpendicular to the base attachment portion 406. A stop member 418, 420 of each of the connecting arms 402, 404 engages the hinge attachment portion 408 of the opposed connecting arm.

Each of the first and second connecting arms 402, 404 includes both a male and female hinge member that are separated by a lateral stabilizing member 426, 428.

IV. SUMMARY

On aspect of the present disclosure relates to a dental modeling system that includes an opposing base, a pin locator, and a dental model base. The opposing base includes an engagement surface configured for mounting an opposing dental model formed from a mold of a person's teeth, and a connecting arm including a hinge member at one end thereof. The a pin locator includes a plurality of elongate pins extending from a base of the pin locator and arranged to align with teeth impressions in the mold when mounting the opposing dental model to the opposing base member. The pin locator also includes a connecting arm extending from the base of the pin locator member of the opposing base member to provide a pivot connection there between. The dental model base includes a primary surface having a plurality of holes, wherein the opposing dental model has been mounted to the opposing base. The dental model base further includes a connecting arm including a hinge member at one end thereof configured for attachment to the hinge member of the opposing base in place of the pin locator hinge member to provide a pivot connection between the dental model base and the opposing base. The plurality of holes of the dental model base can include first and second sets of holes, wherein the first set of holes is aligned linearly along a length of the dental model base and the second set of holes is aligned non-parallel with the first set of holes.

Another aspect of the present disclosure relates to a method of forming a dental model from a mold of person's teeth using a dental modeling system. The dental modeling system includes a first base member, a second base member, and a pin locator. The second base member includes at least one removable pin extending from a support surface thereof, and each of the first and second base members and the pin locator include a hinge member. The method includes coupling the hinge members of the pin locator and the first base member together to form a first pivotal connection, filling a first side of the mold with a first moldable material, arranging the mold with the moldable material in engagement with the support surface of the first base member and pins of the pin locator aligned with teeth impressions in a second side of the mold, and curing the first moldable material. The method further includes decoupling the hinge members of the first base member and the pin locator and coupling the hinge members of the first and second base members together to form a second pivotal connection, filling the second side of the mold with a second moldable material, engaging the second moldable material with the support surface of the second base member, curing the second moldable material, and removing the mold from the cured first and second moldable materials.

Another aspect of the invention relates to a dental articulator that includes first and second base members. The first base member includes a mounting surface, at least one retaining structure extending from the mounting surface, and a connecting arm including a hinge member at one end thereof. The second base member includes a mounting surface having a plurality of holes configured to receive removable pins, wherein the plurality of holes of the first base member including a first set of holes aligned linearly along a length of the first base member and spaced apart with irregular spacing. The second base member also includes an indexing member associated with each of the plurality of holes that extend in a direction away from the mounting surface, and a connecting arm having a hinge member at one end thereof configured for attachment to the hinge member of the first base member to provide a pivotal connection. The second base member can further include a second set of holes arranged in a non-parallel arrangement with the linearly aligned first set of holes.

Another aspect of the present disclosure relates to a pin locator for use with a dental modeling system, wherein the dental modeling system includes at least one model base. The pin locator includes a body member defining a mounting surface, a plurality of fixed locator pins extending from the mounting surface in a spaced apart, generally linear arrangement along a length of the body member, and at least one hole formed in the mounting surface and configured to receive a removable locator pin. The pin locator is configured for attached to the dental model base with a hinged connection, and the locator pins are configured to align with teeth impressions of a dental mold when removably mounting the dental mold to the dental model base.

A further aspect of the present disclosure relates to a dental articulator that includes first and second base members and a hinge structure. The first base member includes a mounting surface and defines a generally rectangular profile when viewed from a top plan view of the mounting surface. The second base member includes a primary surface having a plurality of holes formed therein sized to receive removable pins. The first base member also defines a generally rectangular profile when viewed from a top plan view of the primary surface. The hinge structure couples the first and second base members together in hinged relationship. The hinge structure includes a first connecting arm extending from the first base member, a second connecting arm extending from the second base member, and a stop member configured to stop relative rotation of the first and second base members in at least one rotation direction. The connecting arms extend in a direction substantially parallel with a longitudinal axis of the first and second base member. The connecting arms can be formed integrally with the first and second base members.

Another aspect of the present disclosure relates to a method of forming a dental model. The method includes positioning locator pins of a pin locator in alignment with teeth impressions in a dental mold, and filling the teeth impressions with a curable material. The method further includes engaging pins of a dental model base in engagement with the moldable material, a spacing between pins of the dental model base substantially equal to a spacing between the locator pins, and curing the curable material to form the dental model.

V. CONCLUSION

The above specification, examples and data provide a complete description of the manufacture and use of the composition of the disclosed examples. Since many embodiments of the present disclosure can be made without departing from the spirit and scope of the invention, the invention resides in the claims hereinafter appended.

I claim:

1. A dental modeling system, comprising:
   an opposing base including:
      an engagement surface configured for mounting an opposing dental model formed from a mold of a person's teeth; and
      a connecting arm including a hinge member at one end thereof;
   a pin locator including:
      a plurality of elongate pins arranged linearly in a single row and extending from a base of the pin locator, the elongate pins being arranged to align with teeth impressions in the mold when mounting the opposing dental model to the opposing base; and
      a connecting arm extending from the base of the pin locator and including a hinge member at one end thereof configured for attachment to the hinge member of the opposing base to provide a pivot connection there between, the connecting arm of the pin locator being formed integral as a single piece with the base of the pin locator; and
   a dental model base, including:
      a primary surface having a plurality of holes, the primary surface configured for mounting a dental model formed from the mold after the opposing dental model has been mounted to the opposing base;
      at least one removable pin mounted to the dental model base and having a mounting portion that extends from the primary surface for engagement with the dental model, the mounting portion having a length dimension that is less than a length dimension of the elongate pins; and
      a connecting arm including a hinge member being configured at one end thereof for attachment to the hinge member of the opposing base in place of the pin locator hinge member to provide a pivot connection between the dental model base and the opposing base.

2. The dental modeling system of claim 1, wherein the plurality of holes of the dental model base includes first and second sets of holes, the first set of holes being aligned linearly along a length of the dental model base and the second set of holes being aligned non-parallel with the first set of holes.

3. The dental modeling system of claim 2, wherein the primary surface of the dental model base includes at least two indexing members associated with each hole of the first set of holes, the indexing members being positioned on opposed sides of each hole of the first set of holes.

4. The dental modeling system of claim 3, wherein the indexing members associated with a given hole having different sizes.

5. The dental modeling system of claim 2, wherein the second set of holes includes at least two holes, wherein a separate hole is positioned on opposed sides of the first set of holes.

6. The dental modeling system of claim 5, wherein the second set of holes includes at least four holes, wherein a pair of holes is positioned on opposed sides of the first set of holes and in alignment with an end hole of the first set of holes.

7. The dental modeling system of claim 1, wherein the hinge member of the opposing base and dental model base includes mating stop features configured to restrict rotational movement of opposing base and dental model base relative to each other in at least one rotation direction to provide a parallel arrangement of the engagement surface of the opposing base and the primary surface of the dental model base.

8. The dental modeling system of claim 1, wherein no portion of the connecting arm of the opposing base extends laterally beyond a width of the engagement surface of the opposing base, and no portion of the connecting arm of the dental model base extends laterally beyond a width of the primary surface of the dental model base.

9. The dental modeling system of claim 1, wherein the pin locator includes at least one hole sized to receive a removable tapered pin.

10. The dental modeling system of claim 9, the at least one hole of the pin locator is positioned out of alignment with the linearly arranged elongate pins.

11. The dental modeling system of claim 1, wherein the opposing base is generally rectangular shaped and includes a recessed portion relative to the mounting surface.

12. The dental modeling system of claim 11, wherein the opposing base includes a plurality of protrusions extending from the recessed portion and arranged in rows adjacent to inner sidewalls defined by the recess.

13. A dental modeling system, comprising:
    an opposing base including:
       an engagement surface configured for mounting an opposing dental model formed from a mold of a person's teeth; and
       a connecting arm including a hinge member at one end thereof;
    a pin locator including:
       a single row of elongate pins extending from a base of the pin locator and arranged to align with teeth impressions in the mold when mounting the opposing dental model to the opposing base; and
       a connecting arm extending from the base of the pin locator and including a hinge member at one end thereof configured for attachment to the hinge member of the opposing base to provide a pivot connection there between, the connecting arm of the pin locator being formed integral as a single piece with the base of the pin locator;
       wherein the pin locator is configured for alignment purposes only and not for mounting of a dental model formed from the mold; and
    a dental model base, including:
       a primary surface having a plurality of holes, the primary surface configured for mounting a dental model formed from the mold after the opposing dental model has been mounted to the opposing base;
       at least one removable tapered pin mounted to the dental model base and having a mounting portion that extends from the primary surface for engagement with the dental model; and
       a connecting arm including a hinge member being configured at one end thereof for attachment to the hinge member of the opposing base in place of the pin locator hinge member to provide a pivot connection between the dental model base and the opposing base.

14. The dental modeling system of claim 13, wherein the plurality of holes of the dental model base includes first and second sets of holes, the first set of holes being aligned linearly along a length of the dental model base and the second set of holes being aligned non-parallel with the first set of holes.

15. The dental modeling system of claim 14, wherein the primary surface of the dental model base includes at least two indexing members associated with each hole of the first set of holes, the indexing members being positioned on opposed sides of each hole of the first set of holes.

16. The dental modeling system of claim 15, wherein the indexing members associated with a given hole having different sizes.

17. The dental modeling system of claim 14, wherein the second set of holes includes at least two holes, wherein a separate hole is positioned on opposed sides of the first set of holes.

18. The dental modeling system of claim 17, wherein the second set of holes includes at least four holes, wherein a pair of holes is positioned on opposed sides of the first set of holes and in alignment with an end hole of the first set of holes.

19. The dental modeling system of claim 13, wherein the pin locator includes at least one hole sized to receive a removable tapered pin.

20. The dental modeling system of claim 19, wherein the plurality of elongate pins are arranged linearly, and the at least one hole of the pin locator is positioned out of alignment with the linearly arranged elongate pins.

21. A dental modeling system, comprising:
  an opposing base including:
    a base portion having an engagement surface configured for mounting an opposing dental model formed from a mold of a person's teeth; and
    a connecting arm assembly extending from the base portion and including a hinge member at one end thereof, wherein a total width of the connecting arm assembly is no greater than a maximum width of the base portion;
  a pin locator including:
    a plurality of elongate pins arranged linearly in a single row and extending from a base of the pin locator, the elongate pins being arranged to align with teeth impressions in the mold when mounting the opposing dental model to the opposing base; and
    a connecting arm extending from the base of the pin locator and including a hinge member at one end thereof configured for attachment to the hinge member of the opposing base to provide a pivot connection there between; and
  a dental model base, including:
    a base portion having a upper most surface, an opposing lower most surface, and a plurality of holes defined in the upper most surface, the upper most surface being configured for mounting a dental model formed from the mold after the opposing dental model has been mounted to the opposing base;
    at least one removable pin mounted to the dental model base and having a mounting portion that extends from the upper most surface for engagement with the dental model; and
    a connecting arm extending from the base portion and including a hinge member being configured at one end thereof for attachment to the hinge member of the opposing base in place of the pin locator hinge member to provide a pivot connection between the dental model base and the opposing base.

22. The dental modeling system of claim 1, wherein the connecting arm of the opposing base is formed integral as a single piece with the engagement surface, and the connecting arm of the dental model base is formed integral as a single piece with the primary surface of the dental model base.

23. The dental modeling system of claim 1, wherein the primary surface defines a top surface of the dental model base.

24. The dental modeling system of claim 13, wherein the primary surface defines a top surface of the dental model base.

25. The dental modeling system of claim 21, wherein the upper most surface defines a top surface of the dental model base.

26. The dental modeling system of claim 21, wherein the connecting arm of the pin locator is formed integral as a single piece with the base of the pin locator.

* * * * *